US012618832B2

(12) United States Patent
   Griffiths et al.

(10) Patent No.: US 12,618,832 B2
(45) Date of Patent: May 5, 2026

(54) IDENTIFICATION OF COGNATE PAIRS OF LIGANDS AND RECEPTORS

(71) Applicants: PARIS SCIENCES ET LETTRES, Paris (FR); CENTRE NATIONAL DE LA RECHERCHE SCIENTIFIQUE, Paris (FR); INSTITUT CURIE, Paris (FR); THE PRESIDENT AND FELLOWS OF HARVARD COLLEGE, Cambridge, MA (US); HIFIBIO (HK) LIMITED, Central Hong Kong (CN);
   (Continued)

(72) Inventors: Andrew Griffiths, Paris (FR); Sebastien Amigorena, Paris (FR); Olivier Lantz, Paris (FR); David Weitz, Bolton, MA (US); Philippe Nghe, Saint-Mande (FR); Annabelle Gerard, Palaiseau (FR)

(73) Assignees: PARIS SCIENCES ET LETTRES, Paris (FR); CENTRE NATIONAL DE LA RECHERCHE SCIENTIFIQUE, Paris (FR); INSTITUT CURIE, Paris (FR); THE PRESIDENT AND FELLOWS OF HARVARD COLLEGE, Cambridge, MA (US); HIFIBIO (HK) LIMITED, Central Hong Kong (CN);
   (Continued)

( * ) Notice: Subject to any disclaimer, the term of this patent is extended or adjusted under 35 U.S.C. 154(b) by 1237 days.

(21) Appl. No.: 17/416,287

(22) PCT Filed: Dec. 19, 2019

(86) PCT No.: PCT/EP2019/086334
   § 371 (c)(1),
   (2) Date: Jun. 18, 2021

(87) PCT Pub. No.: WO2020/127754
   PCT Pub. Date: Jun. 25, 2020

(65) Prior Publication Data
   US 2022/0065849 A1     Mar. 3, 2022

(30) Foreign Application Priority Data
   Dec. 19, 2018   (EP) ..................................... 18306741

(51) Int. Cl.
   *G01N 33/53*       (2006.01)
   *A61K 39/00*       (2006.01)
   (Continued)

(52) U.S. Cl.
   CPC ...... *G01N 33/5306* (2013.01); *A61K 39/0011* (2013.01); *C12N 15/1065* (2013.01);
   (Continued)

(58) Field of Classification Search
   None
   See application file for complete search history.

(56) References Cited

U.S. PATENT DOCUMENTS

| 5,962,272 A | 10/1999 | Chenchik et al. |
| 2007/0000342 A1 | 1/2007 | Kazuno |

(Continued)

FOREIGN PATENT DOCUMENTS

| WO | 2004/002627 | 1/2004 |
| WO | 2004/091763 | 10/2004 |

(Continued)

OTHER PUBLICATIONS

International Search Report for PCT/EP2019/086334 dated Mar. 12, 2020, 4 pages.

(Continued)

*Primary Examiner* — Heather Calamita
*Assistant Examiner* — Elizabeth Rose Lafave
(74) *Attorney, Agent, or Firm* — NIXON & VANDERHYE

(57)         ABSTRACT
A method for identifying cognate pairs of a ligand species and a receptor species includes co-compartmentalizing
(Continued)

ligand species and receptor species, forming a set of microreactors, each microreactor including a ligand species and preferably a receptor species; assaying the recognition between ligands and receptors in each microreactor and based on this assay, classifying each microreactor as positive when a ligand species and receptor species in the microreactor recognize one with the other or negative when no ligand species and no receptor species recognize in the microreactor; identifying ligand species and receptor species contained in each positive microreactor; establishing a subset of positive microreactors containing the same receptor species; determining the probability that the ligand species recognizing the receptor species corresponds to the most frequent co-compartmentalized ligand species. If the determined probability exceeds a threshold, identifying as a cognate pair the receptor species and the most frequent co-compartmentalized ligand species.

21 Claims, 3 Drawing Sheets

(71) Applicants: INSTITUT NATIONAL DE LA SANTE ET DE LA RECHERCHE MEDICALE (INSERM), Paris (FR) ECOLE SUPERIEURE DE PHYSIQUE ET DE CHIMIE INDUSTRIELLES DE LA VILLE DE PARIS, Paris (FR);

(73) Assignees: INSTITUT NATIONAL DE LA SANTE ET DE LA RECHERCHE MEDICALE (INSERM), Paris (FR) ECOLE SUPERIEURE DE PHYSIQUE ET DE CHIMIE INDUSTRIELLES DE LA VILLE DE PARIS, Paris (FR);

(51) Int. Cl.
  *C12N 15/10* (2006.01)
  *C12Q 1/6806* (2018.01)

(52) U.S. Cl.
  CPC ..... *C12N 15/1075* (2013.01); *C12N 15/1096* (2013.01); *C12Q 1/6806* (2013.01); *C12Q 2525/149* (2013.01); *C12Q 2535/122* (2013.01); *C12Q 2563/159* (2013.01); *C12Q 2563/179* (2013.01); *C12Q 2565/629* (2013.01)

(56) References Cited

U.S. PATENT DOCUMENTS

| | | | |
|---|---|---|---|
| 2010/0021984 A1 | 1/2010 | Edd et al. | |
| 2011/0223314 A1 | 9/2011 | Zhang et al. | |
| 2013/0011210 A1 | 1/2013 | Toner et al. | |
| 2019/0300934 A1* | 10/2019 | Shiroguchi | ............ C12N 15/09 |

FOREIGN PATENT DOCUMENTS

| | | | |
|---|---|---|---|
| WO | 2008/109176 | 9/2008 | |
| WO | 2013/134162 | 9/2013 | |
| WO | WO-2014153651 A1 * | 10/2014 | ........ B01L 3/502715 |
| WO | 2017/013170 | 1/2017 | |
| WO | WO-2017136727 A2 * | 10/2017 | ............ A61K 31/55 |
| WO | 2018/170013 | 9/2018 | |

OTHER PUBLICATIONS

Written Opinion of the ISA for PCT/EP2019/086334 dated Mar. 12, 2020, 6 pages.
European Search Report for EP 18306741.2 dated Apr. 18, 2019, 8 pages.
Segaliny et al., "Functional TCR T cell screening using single-cell droplet microfludics", Lab on a Chip, Dec. 4, 2018, vol. 18, No. 24, XP055578872, pp. 3733-3749 (17 total pages).

* cited by examiner

IDENTIFICATION OF COGNATE PAIRS OF LIGANDS AND RECEPTORS

CROSS-REFERENCE TO RELATED APPLICATIONS

This application is the U.S. national phase of International Application No. PCT/EP2019/086334 filed Dec. 19, 2019 which designated the U.S. and claims priority to EP 18306741.2 filed Dec. 19, 2018, the entire contents of each of which are hereby incorporated by reference.

BACKGROUND OF THE INVENTION

Field of the Invention

The present invention concerns methods for identifying cognate pairs of ligands and receptors, in particular cognate pairs of T cell receptors and T cell antigens or cognate pairs of B cell receptors and B cell antigens.

Description of the Related Art

Immunotherapy has become an epoch-making and attractive therapeutic modality for cancer, which offers potentially targeted therapy with fewer adverse-effects compared with conventional therapy. One type of immunotherapy is a checkpoint blockade therapy using humanized mAbs specific to CTL antigen 4 (CTLA-4), programmed cell death-1 (PD-1), or its ligand PD-L1. This therapy induced remarkable and durable clinical responses in patients with melanoma, lung, renal, and bladder cancers. However, only a subset of patients (between 20 and 30%) responds to such immune checkpoint therapies and only patients suffering from certain types of cancer.

Accordingly, immunotherapy of cancers using vaccine approaches may be relevant in patients that do not respond to such therapies.

However, very few tumor antigens, which can elicit effective and safe T-cell-mediated antitumor immunity in cancer patients are known. Indeed, such effective tumor antigens need to be overexpressed in cancer tissues, not expressed in normal tissues and be capable of inducing a tumor-antigen specific T-cell response.

Reliable identification of T cell antigens would thus address an unmet need in the field of cancer immunology.

Furthermore, immunotherapy approaches can also potentially be applied to treat autoimmune disease, inflammatory and autoimmune disease, infectious disease and metabolic disease, where efficient and reliable identification of T cell antigens is likewise of great importance.

Autoimmune diseases may also be treated through cell based therapy or by tolerization approach, which also necessitate reliable identification of antigens of interest.

Unfortunately, despite this potential utility, the discovery and characterization of T cell antigen has moved forward very slowly, in particular because of both the vastness of the T cell repertoire and the large number of potential T cell antigens.

Current methods to identify T cell epitopes generally involve isolating T cells, making individual T cell clones and screening a panel of tumor cell lines or expression libraries from the autologous tumor cells (either fresh or from established cell lines) (Boon et al. (1994) Annu Rev Immunol. 12:337-65). This process is labor intensive and inefficient as both T cell clones and tumor cell lines should be established, which is long and is not possible for all tumor types.

More recently, deep sequencing of the tumor DNA together with RNA analysis has allowed the definition and ranking of candidate epitopes using peptide binding prediction algorithms to the specific MHC alleles avoiding the need of establishing tumor cell lines (Gubin et al. (2015) *J. Clin. Invest.* 125:3413-3421). However, for MHC class II restricted epitopes recognized by CD4 T cells, the prediction algorithms are not very reliable. Epitopes can also be identified by proteomic analysis of the acid eluate from immuno-precipitate of MHC class I molecules obtained from the tumor cells, further refining the predictive capacity of the process. In both cases, MHC tetramers loaded with the most likely antigen candidate are then synthesized and used to fluorescently label and isolate potential reactive T cells (Yadav et al. (2014) Nature 515:572-576 and Andersen et al. (2012) *Nat. Protoc.* 7:891-902).

However, making MHC class II tetramers is still challenging for many epitopes.

Alternatively, T cell clones or cell lines expressing cloned TCR are functionally tested against antigen-presenting cells (APC) loaded with synthetic peptides, expression libraries (Gaugler et al. (1994) *J. Exp. Med.* 179:921-930) or transduced with mRNA coding for the candidate epitopes (Holtkamp et al. (2006) *Blood* 108:4009-4017). DNA tagged MHC oligomers technique (Bentzen et al. (2016) *Nat. Biotechnol.* 34:1037-1045) requires prior knowledge of the candidate antigens and is only applicable at the moment for MHC-I restricted epitopes.

However, each method has disadvantages: making T cell clones is extremely labor intensive as is the screening of the resulting clones for antigen specificity; identifying recurrent TCR and/or tumor reactive TCR without cell expansion from bulk population by deconvolution methods is applicable only if only a few TCRs of interest are increased in frequency and enough cells are available; elution of peptides from tumor MHC molecules requires many tumor cells; and bio-informatic analysis of MHC epitope from genomic data requires strong assumptions about the nature of the epitopes.

Altogether, these methods are low-throughput, are based on multi-step processes often requiring the generation of specific reagents (clones, tumor cell lines, MHC tetramers, mRNA, peptides), and are therefore not adapted for unbiased discovery of MHC class I and class II epitopes that may be generated by other mechanisms than mutations or overexpression (e.g. by post-translational modification [notably phosphorylation, ubiquitination, sumoylation . . . ], splicing, insertion/deletions).

There is thus an important need for efficient methods to identify cognate pairs of T cells and T cell antigens, in particular from subjects suffering from cancer, inflammatory and autoimmune disease, infectious disease or metabolic disease.

SUMMARY OF THE INVENTION

The present invention arises from the unexpected finding by the inventors that it is possible to screen rapidly and easily up to thousands, including unlimited set of antigens without any a priori selection, of tumor antigens for their capacity to bind and activate T cells and to reliably identify such cognate pairs of T cell antigen and T cell receptors with a low error rate without further confirmation of the identification.

Furthermore, the identification method designed by the present inventors can be applied to any type of binding pair of ligands and receptors such as B cell antigens and B cell receptors.

The present invention thus concerns a method for identifying cognate pairs of a ligand species and a receptor species, comprising the following steps:

providing a set of ligands, in which each ligand is represented multiple times;
   providing a set of receptors, in which each receptor is preferably represented multiple times;
   creating multiple random sub-sets of said ligands, in which each ligand is represented in multiple, but not all, sub-sets;
   identifying sub-sets of ligands in which a member of the sub-set interacts with a receptor (positive ligand sub-sets);
   identifying the most frequent ligand species present in the positive ligand sub-sets interacting with the same receptor
   determining the probability that the most frequent ligand species corresponds to the cognate ligand for the receptor;
   if the determined probability is greater than a predetermined threshold, identifying as a cognate pair the receptor species and the most frequent ligand species in the positive ligand sub-sets interacting with the receptor.

The present invention more particularly concerns a method for identifying cognate pairs of a ligand species and a receptor species, said method comprising the following steps:

providing a set of ligands, in which each ligand is represented multiple times;
   providing a set of receptors, in which each receptor is preferably represented multiple times;
   co-compartmentalising ligand species and receptor species to form a set of microreactors, each microreactor comprising at least one ligand species and preferably no more than one receptor species;
   assaying the recognition between ligands and receptors in each microreactor and based on this assay, optionally classifying each microreactor as positive when at least one ligand species and the receptor species in the microreactor recognize one with the other or negative when none of the ligand species and no receptor species recognize in the microreactor;
   optionally identifying ligand species and receptor species contained in each positive microreactor;
   optionally establishing a subset of positive microreactors which contain the same receptor species;
   determining the probability that in a given established subset of positive microreactors containing the same receptor species, the ligand species recognized by the receptor species corresponds to the most frequent co-compartmentalized ligand species;
   if the determined probability is greater than a predetermined threshold, identifying as a cognate pair the receptor species and the most frequent co-compartmentalized ligand species.

The present invention also concerns an analyzing system implementing the method of identification according to the invention.

Another object of the invention concerns a composition comprising (i) an isolated antigen identified by the method of identification according to the invention as being part of a TCR/antigen pair, and/or (ii) an isolated T cell expressing a TCR identified by the method of identification according to the invention as being part of a TCR/antigen pair and/or (iii) an isolated TCR identified by the method of identification according to the invention as being part of a TCR/antigen pair and/or (iv) an ex-vivo engineered immune cell expressing either the antigen and/or the TCR identified by the method of identification according to the invention as being part of a TCR/antigen pair, for use in the prevention and/or treatment of cancer, inflammatory and autoimmune disease, autoimmune disease, infectious disease, or metabolic disease.

DESCRIPTION OF THE PREFERRED EMBODIMENTS

Definitions

Unless otherwise defined, scientific and technical terms used in connection with the invention shall have the meanings that are commonly understood by those of ordinary skill in the art.

Generally, nomenclatures utilized in connection with, and techniques of, cell and tissue culture, molecular biology, and protein and oligo- or polynucleotide chemistry and hybridization described herein at those well-known and commonly used in the art.

Standard techniques are used for recombinant DNA, oligonucleotide synthesis and tissue culture. Enzymatic reactions and purification techniques are performed according to manufacturer's specifications or as commonly accomplished in the art or as described herein.

As used herein, the term "nucleic acid" generally refers to at least one molecule or strand of DNA or RNA, comprising at least one nucleobase, such as, for example, a naturally occurring purine or pyrimidine base found in DNA (e.g., adenine "A", guanine "G", thymine "T" and cytosine "C") or RNA (e.g., A, G, uracil "U" and C).

"RNA" refers herein to functional RNA, such as mRNA, tRNA, ncRNA, lncRNA, miRNA, siRNA, piRNA, gRNA, telomerase RNA component, RNAi, CRISPR RNA, circular RNA, enhancer RNA, snoRNA, snRNA and rRNA.

As it will be understood by those skilled in the art, the depiction of a single strand also defines the sequence of the complementary strand. Thus, a nucleic acid also encompasses the complementary strand of a depicted single strand. The term nucleic acid thus encompasses complementary DNA. As it will also be appreciated by those skilled in the art, many variants of a nucleic acid may be used for the same purpose as a given nucleic acid. Thus, a nucleic acid also encompasses substantially identical nucleic acids and complements thereof. As it will also be understood by those skilled in the art, a single strand nucleic acid, such as, a primer, may hybridize to the target sequence under hybridization conditions, preferably stringent hybridization conditions. Thus, a nucleic acid also encompasses a primer that hybridizes under hybridization conditions to a target sequence.

The term "barcoded primer" refers to at least one molecule of about 20 to about 200 nucleobases in length that can function to prime nucleic acid synthesis. In particular, the barcoded primer may be of about 30 to about 150 nucleobases in length, of about 40 to about 100 nucleobases in length, of about 50 to about 90 nucleobases in length, of about 60 to about 80 or 70 nucleobases in length. More particularly, in the context of the invention, a barcoded primer is an oligonucleotide comprising a barcode sequence or barcode set of sequences and a primer sequence, wherein each different primer sequence defines a different specificity of barcoded primer. In one embodiment, the barcoded primer comprises from 5' to 3' a universal primer sequence, a barcode sequence or barcode set of sequences and a primer sequence.

These definitions refer to at least one single-stranded molecule, but in some embodiments encompass also at least one additional strand that is partially, substantially or fully complementary to the at least one single-stranded molecule. Accordingly, in some embodiments said definitions refer to double stranded molecules.

Thus, in one embodiment, a nucleic acid refers to at least one double-stranded molecule that comprises one or more complementary strand(s) or "complement(s)" of a particular sequence comprising a strand of the molecule.

The "barcode sequence" herein refers to a unique nucleic acid sequence that can be distinguished by its sequence from another nucleic acid sequence, thus permitting to uniquely label a nucleic acid sequence so that it can be distinguished from another nucleic acid carrying another barcode sequence.

In one embodiment, the barcode sequence uniquely identifies the nucleic acids contained in a particular microreactor from nucleic acids contained in other microreactors, for instance, even after the nucleic acids are pooled together.

In some embodiments, the barcode sequence may be used to distinguish tens, hundreds, or even thousands of nucleic acids, e.g., arising from cells contained in different microreactors.

In one embodiment, the barcode sequence may be of any suitable length. The barcode sequence is preferably of a length sufficient to distinguish the barcode sequence from other barcode sequences. In one embodiment, a barcode sequence has a length of 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 72, 74, 76, 78, 80, 85, 90 or more nucleotides, such as 50 to 85, 60 to 80, 70 to 80 nucleotides.

In one embodiment, the barcode sequence consists of more than one barcode sequence, wherein the barcoded sequences are different. Such barcode sequence is called herein "set of barcode sequences".

In a related embodiment, the different barcode sequences may be taken from a "pool" of potential barcode sequences. If the barcode sequence consists of more than one barcode sequence, the barcode sequences may be taken from the same, or different pools of potential barcode sequences. The pool of sequences may be selected using any suitable technique, e.g., randomly, or such that the sequences allow for error detection and/or correction, for example, by being separated by a certain distance (e.g., Hamming distance) such that errors in reading of the barcode sequence can be detected, and in some cases, corrected. The pool may have any number of potential barcode sequences, e.g., at least 100, at least 300, at least 500, at least 1,000, at least 3,000, at least 5,000, at least 10,000, at least 30,000, at least 50,000, at least 100,000, at least 300,000, at least 500,000, at least 1,000,000, at least 10,000,000, or at least 100,000,000 barcode sequences.

Methods to join different barcode sequences taken from one "pool" or more than one pool are known to the skilled in the art and include, but are not limited to, the use of ligases and/or using annealing or a primer extension method.

In one embodiment, the barcode sequence is a double stranded or single stranded nucleic acid, or a partially single and double stranded nucleic acid.

A "primer sequence" is typically a short single-stranded nucleic acid, of between 10 to 50 nucleotides in length, designed to perfectly or almost perfectly match a nucleic acid of interest, to be captured and then amplified by typically PCR or reverse transcribed by typically RT. The primer sequences are "specific" to the nucleic acids they hybridize to, i.e. they preferably hybridize under stringent hybridization conditions, more preferably under highly stringent hybridization conditions, and are complementary to or almost complementary to the nucleic acids they hybridize to, also called target sequence.

Typically, the primer sequence serves as a starting point for nucleic acid synthesis, allowing polymerase enzymes such as nucleic acid polymerase to extend the primer sequence and replicate the complementary strand. A primer sequence may be complementary to and hybridize to a target nucleic acid. In some embodiments, a primer sequence is a synthetic primer sequence. In some embodiments, a primer sequence is a non-naturally-occurring primer sequence. A primer sequence typically has a length of 10 to 50 nucleotides. For example, a primer sequence may have a length of 10 to 40, 10 to 30, 10 to 20, 25 to 50, 15 to 40, 15 to 30, 20 to 50, 20 to 40, or 20 to 30 nucleotides. In some embodiments, a primer sequence has a length of 18 to 24 nucleotides.

In one embodiment, the primer sequence is located on the 3' side of the barcoded primer used in context with the invention (i.e. the primer is in a 3' position compared to the barcode sequence).

"Gene" as used herein may be a genomic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA, antisense RNA, lncRNA and piRNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

The term "stringent condition" or "high stringency condition" as used herein corresponds to conditions that are suitable to produce binding pairs between nucleic acids having a determined level of complementarity, while being unsuitable to the formation of binding pairs between nucleic acids displaying a complementarity inferior to said determined level. Stringent conditions are the combination of both hybridization and wash conditions and are sequence dependent. These conditions may be modified according to methods known from those skilled in the art (Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, high stringency conditions are selected to be about 5° C. lower than the thermal melting point (Tm), preferably at a temperature close to the Tm of perfectly base-paired duplexes (Anderson, M. L. M. (1999) *Nucleic acid hybridization*. New York: Bios Scientific Publisher p. 54). Hybridization procedures are well known in the art and are described for example in Ausubel, F. M., Brent, R., Kingston, R. E., Moore, D. D., Seidman, J. G., Smith, J. A., Struhl, K. eds. (1998) Current protocols in molecular biology. V. B. Chanda, series ed. New York: John Wiley & Sons.

High stringency conditions typically involve hybridizing at about 40° C. to about 68° C., wherein said temperature typically corresponds to the highest melting temperature $T_M$ of the nucleic acid to be hybridized with a target sequence, for example, in 5×SSC/5×Denhardt's solution/1.0% SDS, and washing in 0.2×SSC/0.1% SDS at about 60° C. to about 68° C.

As used herein, the term "tissue" refers to a population of cells, generally consisting of cells of the same kind that perform the same, or a similar, function. A tissue can be part of an organ or bone or it can be a loose association of cells, such as cells of the immune system. The tissue can be a healthy tissue or a diseased tissue. In particular, it can be a cancerous tissue or a tissue surrounding a tumor.

As used herein, a "subject" is a mammal, such as a human, but can also be another animal such as a dog, cat, a cow, a sheep, a pig, a horse, a monkey, a rat, a mouse, a rabbit, a guinea pig etc. Preferably, the subject is a human.

In a particular embodiment, the subject suffers from a disease, in particular from cancer, inflammatory and auto-immune disease, infectious disease or metabolic disease.

By "cancer" is meant herein a class of diseases involving neoplasia which include both cancers that involve a solid tumor and those that do not involve a solid tumor (e.g., leukemia).

By "autoimmune disease" is meant herein a wild range of degenerative diseases caused by the immune system attack-ing a person's own cells.

By "inflammatory and autoimmune disease" is meant herein a disease first induced by an inflammatory process, initiated by the activation of T cells by antigen-presenting cells, which subsequently leads to the activation of other inflammatory cells and in turn the release of pro-inflamma-tory cytokines, chemotactic agents and matrix degrading enzymes. Examples of inflammatory and autoimmune dis-eases are well-known from the person skilled in the art and include rheumatoid arthritis, osteoarthritis, osteoporosis, Crohn's disease, ulcerative colitis, multiple sclerosis, peri-odontitis, gingivitis, graft versus host reactions, psoriasis, scleroderma, allopeicia, Sjogren's syndrome, polymyositi-tis, pempligus, uveititis, Addison's disease, atopic dermati-tis, asthma, systemic lupus erythematosus (SLE), nephropa-thy and chronic obstructive pulmonary disease (COPD), diabetic retinopathy and age-related macular degeneration.

By "infectious disease" is meant herein a disease caused by the transmission of a microorganism. In the context of the invention, the term "microorganism" refers equally to viruses, in particular viruses which have a lipid envelope (such as influenza virus, for example), bacteria, parasites, and fungi.

By "metabolic disease" is meant herein any type of disorders in which metabolic errors and imbalances occur and in which the metabolic processes take place in a sub-optimal manner. In a preferred embodiment, the meta-bolic disease is selected from the group consisting of hyper-glycemia, diabetes, in particular type 2 diabetes, obesity, dyslipidemia and hypercholesterolemia. In a particular embodiment, said metabolic disease is diabetes, more par-ticularly type 2 diabetes.

In the context of the invention, the term "cognate pair" of ligands and receptors refers to the pair of a ligand species and the receptor species to which it selectively binds.

By "selectively binding" is meant herein that one member of the pair recognizes and binds to the other member of the pair with greater affinity than to a member of another pair.

By "specifically binding" is meant herein that one mem-ber of the pair recognizes and binds to the other member of the pair and has no detectable binding activity for a member of another pair.

Method of Identification of Cognate Pairs of Ligands and Receptors

Sets of Ligands and Receptors

As used herein, the term "ligand species" refers to a member of a particular recognition pair, which selectively binds to, preferably specifically binds to, the second member of said particular recognition pair (or cognate pair).

As used herein, the term "receptor species" refers to a member of a particular recognition pair, which is selectively bound by, preferably specifically bound to, the second member of said particular recognition pair (or cognate pair).

As such, a molecule that is a ligand can also be a receptor and, conversely, a molecule that is a receptor can also be a ligand since ligands and receptors are defined as binding partners.

As used herein, the term "set of ligands" refers to at least one ligand species, preferably a plurality of ligand species, in particular a plurality of ligand species wherein at least two of the plurality of ligands species are part of distinct recog-nition pairs. Preferably, the set of ligands used in the context of the invention comprises redundant ligand species, i.e. ligand species which are present in the set in multiple copies.

As used herein, the term "set of receptors" refers to at least one receptor species, preferably a plurality of receptor species, in particular a plurality of receptor species wherein at least two of the plurality of receptor species are part of distinct recognition pairs. Preferably, the set of receptors used in the context of the invention comprises redundant receptor species, i.e. receptor species that are present in the set in multiple copies.

In a particular embodiment, the set of receptors is expressed by, or displayed on the surface of a cell (or cells), a bead, in particular engineered APC-like beads as disclosed in Neal et al. (2017) *J. Immunol. Res. Ther.* 2:68-79, or in vitro encoded, as disclosed in Grubaugh et al. (2013) *Vac-cine* 31:3805-3810. Preferably, the set of receptors is expressed by, or displayed on, the surface of a cell (or cells), one cell expressing or displaying a unique receptor species from the set of receptors.

In another particular embodiment, the set of ligands is expressed by, or displayed on the surface of a cell (or cells), a bead, in particular engineered APC-like beads as disclosed in Neal et al. (2017) *J. Immunol. Res. Ther.* 2:68-79, or in vitro encoded, as disclosed in Grubaugh et al. (2013) *Vac-cine* 31:3805-3810. Preferably, the set of ligands is expressed by, or displayed on the surface of a cell (or cells), one cell expressing or displaying one ligand species from the set of ligands or multiple distinct ligand species from the set of ligands, preferably between 2 to 1000, between 5 to 900, between 10 to 800, between 20 to 700, between 30 to 600, between 40 to 500, between 50 to 400 distinct ligand species from the set of ligands, in particular 100 to 350, 150 to 300, or 200 to 250 distinct ligand species from the set of ligands.

In a particularly preferred embodiment, the set of recep-tors is expressed by, or displayed on the surface of a cell (or cells) and the set of ligands is expressed by, or displayed on the surface of another cell (or other cells). Still preferably, the set of receptors is expressed by, or displayed on the surface of a cell (or cells), each cell expressing or displaying a unique receptor species from the set of receptors, and the set of ligands is expressed by, or displayed on the surface of another cell (or other cells), each cell expressing or display-ing multiple distinct ligand species from the set of ligands.

In the context of the invention, the receptors can be for example T cell receptors (TCR, from a TCR/T cell antigen recognition pair), B cell receptors (from a B cell receptor/B cell antigen recognition pair), receptors for stimulatory immune checkpoint molecules (e.g. OX40L from an OX40L/OX40 pair), receptors for inhibitory immune checkpoint molecules (e.g. PD-L1 from a PD-L1/PD-1 pair), cytokine receptors (from a cytokine/cytokine receptor pair), selectins (from a selectin/carbohydrate pair), integrins (from an integrin/member of the immunoglobulin superfamily pair), members of the immunoglobulin superfamily (from a member of the immunoglobulin superfamily/selectin pair, or from a pair comprising two members of the immunoglobulin superfamily), cadherins (from a pair comprising two cadherins), chemokine receptors (from a chemokine/chemokine receptor pair), hormone receptors (from an hormone/hormone receptor pair), growth factor receptors (from a growth factor/growth factor receptor pair), G protein-coupled receptors (GPCR, from a GPCR/corresponding ligand pair) or enzymes (from an enzyme/corresponding substrate pair).

In a preferred embodiment, the set of receptors is a set of T cell receptors.

In the context of the invention, the ligands can be for example T cells antigens (from a TCR/T cell antigen recognition pair), B cell antigen (from a B cell receptor/B cell antigen recognition pair), stimulatory immune checkpoint molecules (e.g. OX40 from an OX40L/OX40 pair), inhibitory immune checkpoint molecules (e.g. PD-1 from a PD-L1/PD-1 pair), cytokines (from a cytokine/cytokine receptor pair), carbohydrates (from a selectin/carbohydrate pair), members of the immunoglobulin superfamily (from a pair comprising two members of the immunoglobulin superfamily), selectin (from a member of the immunoglobulin superfamily/selectin pair), chemokines (from a chemokine/chemokine receptor pair), hormones (from an hormone/hormone receptor pair), growth factors (from a growth factor/growth factor receptor pair), ligands of GPCRs (from a GPCR/corresponding ligand pair) or substrates (from an enzyme/corresponding substrate pair). In a preferred embodiment, the set of ligands is a set of T cell antigens (peptides, glycolipids or small metabolites such as 5-A-RU derivatives), preferably bound to major histocompatibility complex (MHC molecules that can be class I, class II or MR1) or to CD1a, b, c, or d molecules.

T Cell Antigen/T Cell Receptor

In a particular embodiment, the set of receptors is a set of T cell receptors, preferably displayed on the surface of T cells, each T cell preferably having a unique T cell receptor, and the set of ligands is a set of T cell antigens, preferably bound to major histocompatibility complex (MHC) typically displayed on the surface of antigen-presenting cells (APCs), each APC preferably displaying multiple antigen species.

By "T cell antigen" is meant herein a CD4+ T cell antigen or a CD8+ T cell antigen. A "CD4+ T cell antigen" refers to any antigen that is recognized by and triggers an immune response in a CD4+ T cell e.g., an antigen that is specifically recognized by a T cell receptor on a CD4+ T cell via presentation of the antigen or portion thereof bound to a Class II major histocompatibility complex molecule (MHC). A "CD8+ T cell antigen" refers to any antigen that is recognized by and triggers an immune response in a CD8+ T-cell e.g., an antigen that is specifically recognized by a T cell receptor on a CD8+ T cell via presentation of the antigen or portion thereof bound to a Class I major histocompatibility complex molecule (MHC). T cell antigens are generally proteins or peptides, but may be other molecules such as lipids and glycolipids and any derivates thereof.

Tetramers, multimers and derivates thereof, where the antigen specificity is carried by a barcode, or by the gene are also contemplated. The tetramer, or any derivative can be synthesized in the droplet by in vitro transcription translation (IVTT), including the antigen and the corresponding vector. Such vector can include genes encoding expression of a soluble TCR.

Preferably, the set of ligands is a set of T cell antigens bound to major histocompatibility complex (MHC) displayed on the surface of antigen-presenting cells (APCs).

In the context of the invention, the term "antigen-presenting cells" or "APCs" encompasses a heterogeneous group of immunocompetent cells that mediate the cellular immune response by processing and presenting antigens to the T cells. Antigen-presenting cells include, but are not limited to macrophages, dendritic cells, Langerhans cells, B cells, monocyte derived dendritic cell, artificial APCs, engineered APC or other cells expressing MHC class I molecule or MHC class II molecules.

The APCs can be B cells, in particular immortalized B cells such as Epstein-Barr virus (EBV)-immortalized B cells.

In a particular embodiment, the APCs are autologous immortalized B cells from a subject of interest, as defined above, or heterologous immortalized B cells carrying the same MHC as the subject of interest, as defined above.

By "heterologous B cells carrying the same MHC as the subject of interest" is meant herein B cells which do not originate from the subject of interest but which carry the same MHC as the subject of interest.

By "MHC" or "major histocompatibility complex" is meant herein a complex of genes (and the molecules encoded by them) that encode cell-surface molecules required for antigen presentation to T cells and for rapid graft rejection. In humans, the MHC complex is also known as the HLA complex. The proteins encoded by the MHC complex are known as "MHC molecules" and are classified into class I and class II MHC molecules. Class I MHC molecules include membrane heterodimeric proteins made up of an a chain encoded in the MHC associated noncovalently with 32-microglobulin. Class I MHC molecules are expressed by nearly all nucleated cells and have been shown to function in antigen presentation to CD8+ T cells. Class I molecules include HLA-A, -B, and -C in humans. Class II MHC molecules also include membrane heterodimeric proteins consisting of noncovalently associated α and β chains. Class II MHC are known to interact with CD4+ T cells and, in humans, include HLA-DP, -DQ, and DR. The term "MHC restriction" refers to a characteristic of T cells that permits them to recognize antigen only after it is processed and the resulting antigenic peptides are displayed in association with either a class I or class II MHC molecule. Methods of identifying and comparing MHC are well known in the art and are described in Allen et al. (1994) *Human Imm.* 40:25-32; or Santamaria et al. (1993) *Human Imm.* 37:39-50.

In a particular embodiment, each APC expresses or displays at least one T cell antigen, preferably multiple distinct T cell antigens, from the set of T cell antigens, preferably between 2 to 1000, between 5 to 900, between 10 to 800, between 20 to 700, between 30 to 600, between 40 to 500, between 50 to 400 distinct T cell antigens from the set of T cell antigens, in particular 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 distinct T cell antigens from the set of T cell antigens. In a particular embodiment, each APC expresses or displays between 10 to 1000, more preferably, 300 distinct T cell antigen species.

In a particular embodiment, the set of APCs displaying at least one T cell antigen, in particular multiple distinct T cell antigens, is obtained by introducing a library of nucleic acids encoding T cell antigens obtained from a tissue of a subject of interest, as defined above, into autologous APCs from the subject of interest, or heterologous APCs carrying the same MHC as the subject of interest, as defined above.

In another particular embodiment, the set of APCs displaying at least one T cell antigen, in particular multiple distinct T cell antigens, is obtained by introducing into APCs a library of synthetic mRNAs (either as a tandem gene or as single gene) encoding antigens, said mRNAs being identified by sequencing the genome, exome or transcriptome of a tumor and generated by in vitro-transcription.

In another particular embodiment, the set of APCs displaying at least one T cell antigen, in particular multiple distinct T cell antigens, is obtained by introducing into APCs a library of synthetic mRNAs (either as a tandem gene or as single gene) encoding antigens, said mRNAs being identified by sequencing the genome, exome or transcriptome of a tumor and generated by split and pool with the individual mRNA, as exemplified in example 6.

In another particular embodiment, the set of APCs displaying at least one T cell antigen, in particular multiple distinct T cell antigens, is obtained by introducing into APCs a library of synthetic mRNAs (either as a tandem gene or as single gene) encoding antigens, said mRNAs being identified by sequencing the genome, exome or transcriptome of a tumor and generated by using penetratin based delivery of DNA allowing mRNA translation as exemplified in example 7.

In another particular embodiment, the set of APCs displaying at least one T cell antigen, in particular multiple distinct T cell antigens, is obtained by introducing into APCs individual DNA (either as a tandem gene or as single gene encoding antigens, said antigen being identified by sequencing the genome, exome or transcriptome of a tumor) made on beads and transcribed into mRNA and transfected in drop as exemplified in example 8 and 9 and 10.

In another particular embodiment, the set of APCs displaying at least one T cell antigen, in particular multiple distinct T cell antigens, is obtained by introducing into APCs individual DNA (either as a tandem gene or as single gene encoding antigens, said antigen being identified by sequencing the genome, exome or transcriptome of a tumor) made on beads and transcribed into mRNA and transfected or transduced in APC.

In another particular embodiment, the set of APCs displaying at least one T cell antigen, in particular multiple distinct T cell antigens, is obtained by introducing known tagged T cell antigens and/or known tagged nucleic acids encoding T cell antigens, into APCs.

By "tagged" is meant herein bearing a tag such as a nucleic acid of known sequence, a fluorescent dye or a label. Typically, the tag may be a barcode sequence as defined above.

In a particular embodiment, the library of nucleic acids encoding T cell antigens is chemically synthesized based on the sequencing of the patient or pathogen RNA or DNA.

In another particular embodiment, the library of nucleic acids encoding T cell antigens is obtained by amplification (e.g. by PCR) of nucleic acids from a tissue of a subject of interest, as defined above.

In a particular embodiment, the library of nucleic acids encoding T cell antigens is a cDNA library. In another embodiment, the library of nucleic acids encoding T cell antigens is an mRNA library.

A library of nucleic acids encoding T cell antigens obtained from a tissue of a subject of interest can be obtained by methods well-known from the skilled person. In particular, cells, for example MHC-I or MHC-II expressing cells or tumor cells; can be extracted from a tissue of the subject of interest by known techniques such as DNase, protease (such as collagenase) and mechanical digestion. RNAs can be isolated from said cells by techniques well-known to the skilled person such as silica columns or acid phenol techniques. These RNAs can then be reverse transcribed using well-known techniques to obtain a cDNA library. Preferably, the cDNA library is obtained by reverse transcription using primers which hybridize with RNAs. The primers can either prime on all mRNAs by hybridizing to the poly(A) tail (anchored-oligo-dT primers) or be designed to prime only on a specific subset of RNAs or to prime randomly to any RNA.

In a particular embodiment, said library is normalized to reduce biases in the library due to differences in mRNA concentrations.

A range of normalization techniques are well-known to the skilled person, such as duplex-specific nuclease (DSN)-based normalization of cDNA libraries (Bogdanov et al. (2010). *Curr. Protoc. Mol. Biol.* Chapter 5: Unit 5.12.1-27), and normalization of cDNA libraries by mRNA-cDNA hybridization and subtraction (Chen (2003) In S.-Y. Ying (Ed.), *Generation of cDNA Libraries: Methods and Protocols* (pp. 33-40) Totowa, NJ: Humana Press).

In a particular embodiment, the library of nucleic acid encoding T cell antigens contain universal sequences allowing specific amplification and sequencing in subsequent steps of the method of identification of the invention, as defined below.

"Universal sequence" refers to a sequence that can be attached, for example by ligation or any other suitable method (like overlap extension PCR, PCR, primer extension or direct DNA synthesis), to a nucleic acid sequence, particularly in a library of nucleic acid molecules, such that the same sequence is attached to a plurality of different nucleic acid molecules. Such a universal sequence is particularly useful for analyzing multiple samples simultaneously. Examples of universal sequences are universal primers and universal priming sites. A universal priming site contains a "common priming site" to which an appropriate primer can bind to and which can be utilized as a priming site for synthesis of nucleic acid sequences complementary to the nucleic acid sequence attached to the universal primer.

Introduction of a library of nucleic acids encoding T cell antigens into APCs can be carried out by any method well-known from the skilled person, such as by transduction with viral vectors, by electroporation, or by transfection (lipo-, nucleo-fection, nanoparticle based, or using cell-penetrating peptides, for example).

In a particular embodiment, the introduction of the library of T cell antigens-encoding nucleic acids, in particular of the cDNA library of T cell antigens-encoding nucleic acids, into said APCs is performed by transducing said APCs with viral vectors carrying said library.

By "viral vector" is meant herein a virus, or recombinant thereof, capable of encapsulating desirable genetic material and transferring and integrating the desirable genetic material into a target cell, thus enabling the effective and targeted delivery of genetic material both ex vivo and in vivo. Examples of viral vectors include adenovirus vectors, adeno-associated virus vectors, herpes simplex virus vectors, retrovirus vectors, lentivirus vectors, Semliki forest virus vectors, Sindbis virus vectors, vaccinia virus vectors, fowlpox virus vectors, baculovirus vectors and Sendai virus vectors. Preferably, said viral vector is a lentivirus vector.

As will be understood by the skilled person, when the introduction of T cell antigens-encoding nucleic acids into APCs is performed by transduction with viral vectors, the number of distinct T cell antigens expressed or displayed by said APCs depends on the multiplicity of infection (MOI) at which said viral vectors were used to transduce said APCs.

Accordingly, in a particular embodiment, the introduction of the library of T cell antigens-encoding nucleic acids into said APCs is performed by transducing said APCs with viral vectors carrying said library at a multiplicity of infection between 0.01 and 1000, between 0.05 and 900, between 0.1 and 800, between 0.5 and 700, between 1 and 600, between 2 and 500, between 3 and 450, between 4 and 400, between 5 and 350, between 6 and 300, between 7 and 250, between 8 and 200, between 9 and 150, or between 10 and 100, in particular at a multiplicity of infection of 20, 30, 40, 50, 60, 70, 80 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500, thereby generating APCs expressing at least one antigen up to multiple antigens.

In another embodiment, the introduction of the library of T cell antigens-encoding nucleic acids, in particular of the RNA library of T cell antigens-encoding nucleic acids, into said APCs is performed by transfection of APCs with said mRNAs or corresponding DNAs. Such transfection may typically be carried out by lipofection, nucleo-fection, nanoparticle-based transfection or using cell-penetrating peptides (Rádis-Baptista et al. (2017) *Journal of Biotechnology* 252:15-26) such as penetratin, that are covalently coupled to the RNA. The same principle applies for the expression of TCRs by autologous or heterologous T cells, or T cells lines to screen for TCR specificity and/or affinity/avidity towards antigen/MHC complex.

The term "T cell receptor" or "TCR" herein refers to an antigen-recognition molecule present on the surface of T cells (i.e., T lymphocytes). This definition expressly includes the understanding of the term as known in the art, and includes, for example, a receptor that comprises or consists of a disulfide-linked heterodimer of the highly variable alpha or beta chains expressed at the cell membrane as a complex with the invariant CD3 chains, or a receptor that comprises or consists of variable gamma and delta chains expressed at the cell membrane as a complex with CD3 on a subset of T cells. The antigen recognition domain of TCRs is typically composed of an alpha chain and a beta chain, or of a gamma chain and a delta chain, encoded by separate genes.

T-cell receptor genes undergo a unique mechanism of genetic recombination, called V(D)J recombination, that occurs only in developing lymphocytes during the early stages of T cell maturation. It results in the highly diverse repertoire of T cell receptors (TCRs) found on T cells.

Preferably, the set of receptors is a set of TCRs displayed on the surface of T cells.

The term "T cells" or "T lymphocytes" as used generically herein may refer to, for example, CD4$^+$ helper T cells (e.g., TH1, TH2, TH9 and TH17 cells), CD8$^+$ cytotoxic T cells, antigen experienced T cells, naïve T cells, central T cells, effector T cells, CD4$^+$ regulatory/suppressor T cells (Treg cells), natural killer T cells, γδ T cells, and/or auto-aggressive T cells (e.g., TH40 cells), Mucosal Associated Invariant T cells (MAIT), exhausted T cells, memory T cells, central memory T cells, effector memory T cells, tissue resident T cells.

Preferably, in the set of T cells displaying TCRs, each T cell expresses or displays a unique T cell receptor (TCR).

In a particular embodiment, the T cells of the set of T cells displaying TCRs, are derived from the same subject of interest as the library of nucleic acids encoding T cell antigens, as defined above, used to obtain the set of APCs displaying T cell antigens. In particular, this embodiment facilitates the detection of private T cell antigens.

By "private antigen" is meant herein an antigenic specificity restricted to one or a few individuals.

In another particular embodiment, the T cells of the set of T cells displaying TCRs, are not derived from the same subject of interest as the library of nucleic acids encoding T cell antigens, as defined above, used to obtain the set of APCs displaying T cell antigens. In particular, this embodiment facilitates the detection of public T cell antigens.

By "public antigen" is meant herein an antigen that is present in more than 5% more particularly in more than 10% of a population.

In a particular embodiment, the T cells of the set of T cells displaying TCRs are activating to allow their expansion after being collected from the subject.

B Cells Receptors/B Cells Antigens

In another particular embodiment, the set of receptors is a set of B cell receptors (BCR or antibodies) and the set of ligands is a set of B cell antigens.

As used herein, the term "BCR" refers to a transmembrane receptor protein located on the outer surface of B cells. The receptor's binding moiety is composed of a membrane-bound antibody that, like most antibodies, has a unique and randomly determined antigen-binding site (see V(D)J recombination). When a B cell is activated by its first encounter with an antigen that binds to its receptor (its "cognate antigen"), the cell proliferates and differentiates to generate a population of antibody-secreting plasma B cells and memory B cells.

The term "antibody" refers to immunoglobulin molecules and immunologically active portions of immunoglobulin molecules, i.e., molecules that contain an antigen binding site which immunospecifically binds an antigen. As such, the term antibody encompasses not only whole antibody molecules, but also antibody fragments as well as variants of antibodies, including derivatives such as humanized antibodies. In certain conventional antibodies, two heavy chains are linked to each other by disulfide bonds and each heavy chain is linked to a light chain by a disulfide bond. There are two types of light chain, lambda (λ) and kappa (κ). There are five main heavy chain classes (or isotypes) which determine the functional activity of an antibody molecule: IgM, IgD, IgG, IgA, IgE and IgY. Each chain contains distinct constant region sequences. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non hypervariable or framework regions (FR) influence the overall domain structure and hence the combining site. Complementarity determining regions (CDRs) refer to amino acid sequences which, together, define the binding affinity and specificity of the natural Fv region of a native immunoglobulin binding-site. The light and heavy chains of an immunoglobulin each have three CDRs, designated L-CDR1, L-CDR2, L-CDR3 and H-CDR1, H-CDR2, H-CDR3, respectively. Therefore, an antigen-binding site includes six CDRs, comprising the CDR set from each of a heavy and a light chain V region. Framework Regions (FRs) refer to amino acid sequences interposed between CDRs, i.e. to those portions of immunoglobulin light and heavy chain variable regions that are relatively conserved among different immunoglobulins in a single species, as defined by Kabat, et al. (Sequences of Proteins of Immunological Interest (National Institutes of Health, Bethesda, Md., 1991).

The term antibody further denotes single chain antibodies, for instance Camelidae antibodies, or nanobodies or $V_{HH}$.

Antibody genes generally undergo a unique mechanism of genetic recombination, called V(D)J recombination, that occurs only in developing lymphocytes during the early stages of B cell maturation. The antibody genes may be further subjected to somatic hypermutation, and the combination of V(D)J recombination and somatic hypermutation results in the highly diverse repertoire of antibodies/immunoglobulins (Igs) found on B cells.

In a particular embodiment, when the set of receptors is a set of B cell receptors, said B cell receptors are displayed by B cells.

Co-Compartmentalisation

By "co-compartmentalising" ligand species and receptor species is meant herein forming a plurality of microreactors, each microreactor separating a group of ligand species and/or receptor species, preferably a group of at least one ligand species and optionally at least one receptor species, from the remaining ligand species and receptor species provided by the set of ligands and receptors.

In the context of the invention, the co-compartmentalisation step may be carried out by any suitable method, such as by microfluidics, flow cytometry cell based sorting, limiting dilution.

In a particular embodiment, the microreactors are wells or microfabricated wells.

In another particular embodiment, the microreactors are aqueous droplets, in particular in a continuous immiscible phase.

A "droplet" generally refers to a measure of volume and further refers in context of the present invention, to an isolated portion of a first fluid that is surrounded by a second fluid. It is to be noted that a droplet is not necessarily spherical, but may assume other shapes as well, for example, depending on the external environment.

Preferably, each droplet has a volume at least equal to the volume of two mammalian cells.

In another particular embodiment, the microreactors are microcapsules. The microcapsules can refer to a measure of volume and further refers in context of the present invention, to an isolated portion of a first coating material that surround a second material. It is to be noted that a microcapsule is not necessarily spherical, but may assume other shapes as well, for example, depending on the external environment. A "microcapsule" generally refers to hollow microparticle composed of a solid shell surrounding a core-forming space available to permanently or temporarily entrapped substances. The substances can be drugs, pesticides, dyes, cells, combinations thereof and similar materials. enclose solids, liquids, or gases inside a micrometric wall made of hard or soft soluble film. The coating materials generally used for coating are ethyl cellulose, polyvinyl alcool, gelatin, sodium alginate.

Preferably, each microcapsule has a volume at least equal to the volume of two mammalian cells.

In another particular embodiment, the microreactors are microbeads. The microbeads can refer to a measure of volume and further refers in context of the present invention, to an isolated portion of a first semi-solid material that is surrounded by a fluid, either permeant or not to the semi-solid bead. It is to be noted that a microbead is not necessarily spherical, but may assume other shapes as well, for example, depending on the external environment. A "microbead" generally refers to a semi-solid porous or not structure, occupying the whole volume available to permanently or temporarily entrapped substances. The substances can be drugs, pesticides, dyes, cells, combinations thereof and similar materials. enclose solids, liquids, or gases inside a micrometric wall made of hard or soft soluble film. The materials generally used for forming microbeads include polymers like agarose, acrylamide, sodium alginate.

Preferably, each microbead has a volume at least equal to the volume of two mammalian cells.

It is understood that cells can be encapsulated in microcapsules or microbeads before these achieve their transformation of droplet into microcapsules or microbeads.

The average volume of a mammalian cell is well-known to the skilled person and is typically of about 0.002 nL.

In a particular embodiment, each droplet or microcapsule or microbead has a volume of less than 20 nL. In one embodiment, each droplet has a volume of less than 15 nL, less than 10 nL, less than 9 nL, less than 8 nL, less than 7 nL, less than 6 nL, less than 5 nL, less than 3 nL, less than 2.5 nL, less than 2 nL, less than 1.5 nL, less than 1 nL, less than 0.5 nL, les than 0.2 nL, less than 0.1 nL, less than 0.05 nL, for example 20 pL to 3 nL, 30 pL to 1 nL, 40 pL to 500 µL, 50 pL, to 250 µL, 60 pL to 100 pL, or 0.1 nL to 3 nL, 0.5 nL to 3 nL, 1 nL to 3 nL, typically, 0.1 nL, 0.5 nL, 1 nL, 1.2 nL, 1.4 nL, 1.6 nL, 1.8 nL, 2.0 nL, 2.2 nL, 2.4 nL, 2.6 nL, 2.8 nL, 3 nL.

Such droplets or micro-capsule or micro-bead may be prepared by any technique well-known from the skilled person, in particular by microfluidics technique.

As it will be understood by the skilled in the art and as further explained below, the number of ligands and receptors, in particular of T cell antigens-displaying APCs and TCR displaying T cells, co-compartmentalized in one microreactor, for instance a droplet, follows a probability distribution, for example a Poisson distribution, and depends on, for example, the concentration of the first type of cells in the first fluid, the concentration of the second type of cells in the second fluid, the geometry of the main channel and the secondary channel, the injection parameters of the first fluid, of the second fluid and of the carrier fluid used.

If the ligands and/or receptors are displayed on cells or particles, the distribution of cells or particles, and hence also the distribution of ligands and/or receptors, will typically follow a Poisson distribution. However, if the microreactors are droplets, a variety of microfluidic techniques, familiar to the skilled person, allow distributions other than Poisson distribution, in particular distributions in which a higher fraction of droplets contains single cells/particles. These techniques include methods consisting in ordering the particles/cells before compartmentalization into droplets using inertial forces and mediated by secondary flows such as Dean flow (see Edd et al. (2008) *Lab Chip* 8:1262-1264; Kemna et al. *Lab Chip* (2012) 12:2881-2887, Lagus and Edd (2013) *RSC Advances* 3:20512-20522, Schoeman et al. (2014) *Electrophoresis* 35:385-392, Schoeman et al. (2018) *Scientific Reports* 8:3714, US 2013/011210, US 2010/021984 and US 2011/0223314), methods consisting in the isolation/sorting of the droplet containing a single cell/particle or a pair of cells/particles to reduce the number of droplets to analyze/measure (see Hu et al. (2015) *Lab Chip* 15:3989-3993; Chung et al. (2017) *Lab Chip* 17:3664-3671 and Shembekar et al. (2018) *Cell Reports* 22:2206-2215), methods consisting in forcing the cells/particles to flow in a narrow bottleneck to reduce chances of encapsulating multiple cells/particles of the same sample (see Ramji et al. (2014) *Biomicrofluidics* 8:034104), methods consisting in the production of droplets on demand when a cell/particle is passing in front of the nozzle (see Schoendube et al. (2015) *Biomicrofluidics* 9:014117; Leibacher et al. (2015) *Biomicrofluidics* 9:024109 and Yusof et al. (2011) *Lab. Chip* 11:2447-2454).

Accordingly, in a particular embodiment, a plurality of receptor species, in particular of TCR displaying T cells comprised in an aqueous composition are co-compartmentalized with a plurality of ligands, in particular of antigen-displaying APCs, into a plurality of microreactors, in particular in a plurality of microfluidic droplets, and the number of receptor species, in particular of TCR displaying T cells, co-compartmentalized into one microreactor, in particular co-compartmentalised in one droplet follows, depending on the parameters used, a probability distribution, in particular a Poisson distribution. The parameters can be adapted to obtain, for instance, most microreactors having either 1 or 0 receptor, in particular TCR displaying T cell, in it, thus minimizing the number of compartments containing several receptors.

As shown by the inventors, the parameters used to co-compartmentalize receptor species, in particular TCR displaying T cells, with ligand species, in particular antigen-displaying APCs, can be adapted to obtain at least some of the microreactors comprising a single receptor species, in particular a single TCR displaying T cell.

Similarly, the parameters used to co-compartmentalize receptor species, in particular TCR displaying T cells, with ligand species, in particular antigen-displaying APCs, can be adapted to obtain at least some of the microreactors comprising a single ligand species, in particular a single antigen-displaying APC.

In a particular preferred embodiment, a set of microreactors is created, each comprising at least one ligand species, in particular at least one T cell antigen, more particularly at least one T cell antigen-displaying APC, and at least one receptor species, in particular at least one TCR, more particularly at least one TCR displaying T cell.

As will be understood by the skilled person, some microreactors may however be created which do not include any receptor species.

Preferably, a set of microreactors is created, each comprising at least one ligand species, in particular at least one T cell antigen, more particularly at least one T cell antigen-displaying APC, and one or a small number of receptor species, in particular one or a small number of TCR, more particularly one or a small number of TCR displaying T cells.

By "small number" is meant herein less than 10, such as 10, 9, 8, 7, 6, 5, 4, 3, 2 or 1.

In another preferred embodiment, a set of microreactors is created, each comprising one or a small number of ligand species, in particular one or a small number of T cell antigens, more particularly one or a small number of T cell antigen-displaying APC, and at least one receptor species, in particular at least one TCR, more particularly at least one TCR displaying T cell.

In a still preferred embodiment, a set of microreactors is created, each comprising one or a small number of ligand species, in particular one or a small number of T cell antigens, more particularly one or a small number of T cell antigen-displaying APC, and one or a small number of receptor species, in particular one or a small number of TCR, more particularly one or a small number of TCR displaying T cells.

In a preferred embodiment, a set of microreactors is created, each comprising one ligand species, in particular one T cell antigen, more particularly one T cell antigen-displaying APC, and one receptor species, in particular one TCR, more particularly one TCR displaying T cell.

In a particularly preferred embodiment, a set of microreactors is created, each comprising multiple ligand species, in particular multiple T cell antigens, more particularly one APC displaying multiple T cell antigens or multiple APCs displaying single (or multiple) T cell antigens, and one receptor species, in particular one TCR, more particularly one TCR displaying T cell.

Accordingly in one embodiment, the set of microreactors is formed by co-compartmentalization of ligand species, in particular antigen-displaying APCs, and receptor species, in particular TCR-displaying T cells, at a frequency of 1 to 20 000 microreactors per second, such as 1 to 15 000 microreactors per second, 1 to 10 000 microreactors per second, 1 to 9000 microreactors per second, 1 to 8000 microreactors per second, 1 to 7000 microreactors per second, 1 to 6000 microreactors per second, 1 to 5000 microreactors per second, 1 to 4000 microreactors per second, 1 to 3000 microreactors per second, 1 to 2000 microreactors per second, 1 to 1000 microreactors per second, 1 to 800 microreactors per second, 1 to 700 microreactors per second, 1 to 600 microreactors per second, 1 to 500 microreactors per second, 1 to 400 microreactors per second, 1 to 300 microreactors per second, 1 to 200 microreactors per second, 1 to 100 microreactors per second, 1 to 80 microreactors per second, 1 to 70 microreactors per second, 1 to 50 microreactors per second, for example 10 to 300 microreactors per second, 50 to 300 microreactors per second, 100 to 300 microreactors per second, 150 to 300 microreactors per second, 150 to 250 microreactors per second, 175 to 250 microreactors per second, typically, 1 to 1000 microreactors per second, preferably 175 to 250 microreactors per second.

The set of microreactors, in particular the set of microfluidic droplets, may be obtained by any suitable technique. In particular, the set of microreactors may be formed by:
  providing a first fluid source, the first fluid comprising a suspension of a set of receptors as defined above,
  providing a second fluid source, the second fluid comprising a suspension of a set of ligands as defined above;
  providing a carrier fluid, the carrier fluid being immiscible with the first fluid and the second fluid,
  injecting the carrier fluid in a main channel of a chip,
  generating a flow of microreactors, in particular droplets, in the carrier fluid by injecting the second fluid and the first fluid in at least a secondary channel of the chip, the secondary channel opening in the main channel, each generated microreactor, in particular droplet, comprising a mix of the first fluid and the second fluid, wherein the concentration of the receptors in the first fluid, the concentration of the ligands in the second fluid, the geometry of the main channel and the secondary channel, the injection parameters of the first fluid, of the second fluid and of the carrier fluid are adapted such that each microreactor, in particular droplet, comprises at least one receptor species, preferably only a single receptor species, and at least one ligand species and preferably presents a volume of less than 20 nL.

Alternatively, the set of microreactors may be formed by:

providing a first fluid source, the first fluid comprising a suspension of a set of pre-formed receptors and ligands as defined above, providing optionally a second fluid source, the second fluid comprising reagents for detection as defined above, providing a carrier fluid, the carrier fluid being immiscible with the first fluid and the second fluid.

In one embodiment, the first and second fluid sources are organized in the form of a junction.

The junction may be, for instance, a T-junction, a Y-junction, a channel-within-a-channel junction (e.g., in a coaxial arrangement, or comprising an inner channel and an outer channel surrounding at least a portion of the inner channel), a cross (or "X") junction, a flow-focusing junction, or any other suitable junction for creating droplets. See, for example, International Patent Application No. PCT/US2004/010903, filed Apr. 9, 2004, entitled "Formation and Control of Fluidic Species," by Link, et ah, published as WO 2004/091763 on Oct. 28, 2004, or International Patent Application No. PCT/US2003/020542, filed Jun. 30, 2003, entitled "Method and Apparatus for Fluid Dispersion," by Stone, et ah, published as WO 2004/002627 on Jan. 8, 2004.

In some embodiments, the junction may be configured and arranged to produce substantially monodisperse droplets.

The amount of receptor species/droplet may also be referred to as loading rate.

For example, the average loading rate may be less than about one receptor species/droplet, less than about 0.9 receptor species/droplet, less than about 0.8 receptor species/droplet, less than about 0.7 receptor species/droplet, less than about 0.6 receptor species/droplet, less than about 0.5 receptor species/droplet, less than about 0.4 receptor species/droplet, less than about 0.3 receptor species/droplet, less than about 0.2 receptor species/droplet, less than about 0.1 receptor species/droplet, less than about 0.05 receptor species/droplet, less than about 0.03 receptor species/droplet, less than about 0.02 receptor species/droplet, or less than about 0.01 receptor species/droplet. In some cases, lower receptor species loading rates may be chosen to minimize the probability that a droplet will be produced having two or more receptor species in it. Thus, for example, at least about 50%, at least about 60%, at least about 70%, at least about 80%, at least about 90%, at least about 95%, at least about 97%, at least about 98%, or at least about 99% of the droplets may contain either no receptor species or only one receptor species.

The at least some microreactors may further comprise, in context of the present invention, a reverse transcriptase and barcoded primers, as further defined herein below.

Recognition Assay and Classification

By "recognition" is meant herein a binding between a ligand species and a receptor species, preferably inducing a particular reaction by the ligand species and/or the receptor species.

As will be understood by the skilled person, the reaction induced by a recognition between a ligand species and a receptor species will depend on the particular ligands and receptors considered. For example, the recognition between a T cell antigen and its corresponding TCR displayed by a T cell will induce the activation of said T cell. Similarly, the recognition between a B cell antigen and its corresponding B cell receptor displayed by a B cell will induce the activation of said B cell.

Accordingly, the assay used to determine the recognition between a ligand species and a receptor species will depend on the particular ligands and receptors considered.

In a particular embodiment, when the receptor species of the set of receptors are displayed by cells, the recognition between ligands and receptors in each microreactor is assayed by determining if a cellular response is induced in said microreactor, the microreactor being classified as positive (recognition between a ligand species and a receptor species in the microreactor) when an induced cellular response is determined in said microreactor, and the microreactor being classified as negative (no recognition between a ligand species and a receptor species in the microreactor) when no induced cellular response is determined in said microreactor.

More particularly, when the set of receptors is TCR displaying T cells and the set of ligands is T cell antigen-displaying APCs, the recognition between ligands and receptors is assayed by determining if T cell activation is induced in said microreactor, the microreactor being classified as positive (recognition between a ligand species and a receptor species in the microreactor) when an induced T cell activation is determined in said microreactor, and the microreactor being classified as negative (no recognition between a ligand species and a receptor species in the microreactor) when no induced T cell activation is determined in said microreactor.

By "T cell activation" is meant herein the regulated series of events induced by the recognition of antigen whatever its chemical nature with a TCR which results in activation, differentiation, proliferation and acquisition of the T cell immunologic function by the TCR-displaying T cell. As well-known from the skilled person, signaling cascades initiated by TCR activation include the inositol tri-phosphate/$Ca^{2+}$, diacylglycerol/protein kinase C, Ras/mitogen-activated protein kinase, and the PI 3-K pathways. Components of these pathways transmit information into the nucleus to activate the genes that code for a variety of secreted factors, such as IL-2, IL-4, IL-7, IL-9, IL-10, TNF-$\alpha$, and interferon-$\gamma$, to activate the genes that code for a variety of cell surface expressed activation markers, such as CD137, CD40L and CD69, and to induce Caspase 3/7 pathway, associated with the proliferation, maturation, and function of cellular components of the immune system.

Assays to determine T cell activation are well-known from the skilled person and include among others, detection of an upregulation of CD69, CD137, CD134 (OX40) or CD40L, detection of cytokine secretion, detection of the induction of Caspase 3/7 pathway, as well as the secretion of perforin or granzyme, or TNF-$\alpha$, and interferon-$\gamma$.

T cell activation can also be detected by sequencing of T cell mRNA using barcoded cDNA primers to detect mRNAs expression patterns characteristic specific of activated T cells. These cDNA primers typically comprise the same barcode sequence as the ligand-specific and receptor-specific cDNA barcoded primers in the same microreactor and thus the cDNAs comprise the same barcode sequences as comprised in the ligand and receptor cDNAs, allowing the ligands and receptors in positive droplets (which contain activated T cells) to be identified by sequencing. The cDNA primers may, optionally, also comprise Unique Molecular Identifiers (UMIs) (Kivioja et al. (2012). *Nat. Methods*, 9, 72-74; Islam et al. (2014). *Nat. Methods*, 11, 163-166), to facilitate quantification and normalization of mRNA expression. The number of reads, or, optionally, the number of UMIs, is used to quantify and normalize the mRNA expression.

Similarly, when the set of receptors is B cell receptor displaying B cells and the set of ligands is B cell antigens, the recognition between ligands and receptors is assayed by determining if B cell activation is induced in said microreactor, the microreactor being classified as positive (recognition between a ligand species and a receptor species in the microreactor) when an induced B cell activation is determined in said microreactor, and the microreactor being classified as negative (no recognition between a ligand species and a receptor species in the microreactor) when no induced B cell activation is determined in said microreactor.

By "B cell activation" is meant herein a process or activity that causes B cells to exhibit a phenotype of an activated B cell, and "activated B cell" describes B cells that can exhibit some of the following phenotypes: B cell activation can be measured by any methods known in the art to identify antibody production (induction of >50 fold increase of expression, up to 300 times) and surface expression versus secretion, antigen specificity, expression of CD138/CD38, high reticulum endoplasmic reticulation or abundance, antigen-mediated activation, T cell dependent activation, T cell-independent activation, (see Blood. 2003; 102:592-600, Blood. 2002; 99:2905-2912, and Blood. 2010; 116(18): 3445-3455) etc.

Assays to determine B cell activation are well-known from the skilled person.

B cell activation can also be detected by sequencing of B cell mRNA using barcoded cDNA primers to detect mRNAs expression patterns characteristic specific of activated B cells. These cDNA primers typically comprise the same barcode sequence as the ligand-specific and receptor-specific barcoded cDNA primers in the same microreactor and thus the cDNAs comprise the same barcode sequences as comprised in the ligand and receptor cDNAs, allowing the ligands and receptors in positive droplets (which contain activated B cells) to be identified by sequencing. The cDNA primers may, optionally, also comprise Unique Molecular Identifiers (UMIs), to facilitate quantification of mRNA expression. The number of reads, or, optionally, the number of UMIs, is used to quantify mRNA expression.

In a particular embodiment, assay reagents are added to the microreactors. Preferably, said assay reagents are co-compartmentalized with said ligand species and said receptor species during the co-compartmentalization step.

For example, when the microreactors are microfluidic droplets, said assay reagents can be included in the first fluid and/or the second fluid used for the formation of said droplets. Alternatively, said assay reagents may be provided through a third fluid.

Reagents can also be added to pre-formed droplets by a variety of methods known to the skilled person, including passive droplet coalescence (see Mazutis et al. (2009). *Lab Chip*, 9 (18), 2665-2672; Mazutis & Griffiths (2012) *Lab Chip*, 12:1800-1806), droplet coalescence driven by local heating from a focused laser (Baroud et al. (2007). *Lab Chip* 7:1029-1033) or using electric forces (Chabert et al. (2005) *Electrophoresis*, 26:3706-3715; Ahn et al. (2006) *Appl. Phys. Lett.*, 88:264105; Link et al. (2006) *Angew. Chem., Int. Ed.*, 45:2556-2560; Priest et al. (2006) *Appl. Phys. Lett.*, 89:134101), or by injection of liquids into pre-formed droplets, for example using electrical forces (picoinjection) (Abate et al. (2010) *Proc. Nat. Acad. Sci. USA*, 107:19163-19166).

As will be understood by the skilled person, said assay reagents will depend on the particular recognition assay carried out.

In a particular embodiment, said assay reagents include a reporter reagent enabling the direct sorting of positive microreactors by detection techniques, as defined below.

Based on the results of the assay, which is performed in each microreactor, each microreactor can be classified as positive or negative.

In a particular embodiment, positive microreactors can be separated from negative microreactors, thereby forming a group of positive microreactors.

Said separation can be carried out by any technique well-known from the skilled person, which will depend on the type of microreactors used. In particular, said separation may be carried out by sorting of the microreactors, in particular of the microfluidic droplets, for example by detecting a reporter reagent. Said separation may also be carried out by sorting of the microreactors by flow cytometry.

In a preferred embodiment, when the microreactors are droplets, the droplets will be sorted in a microfluidic device by dielectrophoresis (Ahn et al. (2006) *Appl. Phys. Lett.* 88:024104) or using surface acoustic waves (Franke et al. (2009) *Lab Chip* 9:2625-2627), triggered, for example, by detecting a fluorescent signal in the droplets (Baret et al. (2009) *Lab Chip*, 9:1850-1858) or using magnetophoretic forces or using pneumatic controllers (see Xi et al. (2017) *Lab Chip* 17:751-771).

Alternatively, based on the classification of the microreactors as positive or negative, a subset of positive microreactors can be only intellectually established, without physically forming a group of positive microreactors.

Optional Additional Reagents and Treatments of Microreactors

In a particular embodiment, said microreactors, in particular said positive microreactors, include additional reagents.

Additional reagents typically include a reverse transcriptase (RT), a cell lysis buffer, deoxynucleotide triphosphates (dNTPs) and a plurality of barcoded primers specific for a nucleic acid sequence encoding the ligand or ligand candidate and of barcoded primers specific for a nucleic acid sequence encoding the receptor, as defined below.

When the ligand is a tagged ligand, as defined above, the barcoded primers specific for a nucleic acid sequence encoding the ligand may be barcoded primers specific for a nucleic acid sequence encoding the tag of said ligand. Similarly, when the receptor is a tagged receptor, as defined above, the barcoded primers specific for a nucleic acid sequence encoding the receptor may be barcoded primers specific for a nucleic acid sequence encoding the tag of said receptor.

Accordingly, in a particular embodiment, additional reagents are added to the microreactors, in particular to the positive microreactors, said additional reagents comprising at least a reverse transcriptase (RT), deoxynucleotide triphosphates (dNTPs), and a plurality of barcoded primers specific for a nucleic acid sequence encoding the ligand (or the ligand's tag) and of barcoded primers specific for a nucleic acid sequence encoding the receptor (or the receptor's tag) and optionally a cell lysis buffer, wherein the barcoded primers specific for the ligand (or the ligand's tag)-encoding nucleic acid sequence comprise a primer sequence specific for the ligand (or the ligand's tag)—encoding nucleic acid sequence and a barcode sequence or barcode set of sequences, wherein the barcoded primers specific for the receptor (or the receptor's tag)—encoding nucleic acid sequence comprise a primer sequence specific for the receptor (or the receptor's tag)—encoding nucleic acid sequence and a barcode sequence or barcode set of sequences, and wherein the barcode sequence or barcode set of sequences contained in a microreactor is distinguishable from the barcode sequence or barcode set of sequences contained in other microreactors, but the barcoded primers specific for the ligand (or the ligand's tag)—encoding nucleic acid sequence and for the receptor (or the receptor's tag)—encoding nucleic acid sequence contained in a given microreactor carry a common barcode sequence or barcode set of sequences.

Accordingly, in a particular embodiment, additional reagents are added to the microreactors, in particular to the positive microreactors, said additional reagents comprising at least a reverse transcriptase (RT), deoxynucleotide triphosphates (dNTPs), and a plurality of primers, being optionally barcoded, that will serve as template for template switch reaction (as described in U.S. Pat. No. 5,962,272), where either free floating specific primers for a nucleic acid sequence encoding the ligand (or the ligand's tag) and of barcoded primers specific for a nucleic acid sequence encoding the receptor (or the receptor's tag) would be added and/or a polydT primers and/or random primer would be optionally added and optionally a cell lysis buffer, wherein the primers, being optionally barcoded, specific for the template switching reaction comprise a primer sequence known for people skilled in the art to associate with non templated nucleotides generated during the RT by the reverse transcriptase at the 3' end of the cDNA, typically triple Cytosine (see Zajac et al. (2013) *PLOS ONE* 8: e85270), wherein the primers, being optionally barcoded, specific for the non templated nucleotide (typically three cytosines) comprise a primer sequence specific for non templated nucleotide and a barcode sequence or barcode set of sequences, and wherein the barcode sequence or barcode set of sequences contained in a microreactor is distinguishable from the barcode sequence or barcode set of sequences contained in other microreactors, but the barcoded primers specific for the non templated nucleotides contained in a given microreactor carry a common barcode sequence or barcode set of sequences.

When the receptor is a TCR, the nucleic acid sequence encoding the receptor is preferably a nucleic acid sequence encoding an alpha T cell receptor, a beta T cell receptor, a gamma T cell receptor or a delta T cell receptor.

When the receptor is an antibody displaying B cell, the nucleic acid encoding the receptor is preferably a nucleic acid sequence encoding the antibody heavy chain variable domain or the antibody light chain variable domain.

When the receptor, is constituted of several polypeptides, each encoded by a separate gene, several distinct barcoded primers each specific for the nucleic acid sequence encoding one of said polypeptides are preferably added. In other words, when the receptor is constituted of a number n of polypeptides, each encoded by a separate gene, a first barcoded primer comprising a primer sequence specific for the nucleic acid sequence encoding a first polypeptide of said receptor is added, a second barcoded primer comprising a primer sequence specific for the nucleic acid sequence encoding a second polypeptide of said receptor is added, . . . and a $n^{th}$ barcoded primer comprising a primer sequence specific for the nucleic acid encoding the $n^{th}$ polypeptide of said receptor is added.

Similarly, when the ligand is constituted of several polypeptides, each encoded by a separate gene, several distinct barcoded primers each specific for the nucleic acid sequence encoding one of said polypeptides are preferably added. In other words, when the ligand is constituted of a number n of polypeptides, each encoded by a separate gene, a first barcoded primer comprising a primer sequence specific for the nucleic acid sequence encoding a first polypeptide of said ligand is added, a second barcoded primer comprising a primer sequence specific for the nucleic acid sequence encoding a second polypeptide of said ligand is added, . . . and a $n^{th}$ barcoded primer comprising a primer sequence specific for the nucleic acid encoding the $n^{th}$ polypeptide of said ligand is added.

In a particular embodiment, typically when the receptor is constituted of two polypeptides, in particular of two chains, encoded by two separate genes, the barcoded primers specific for a nucleic acid sequence encoding the receptor are two different barcoded primers, each specific for a nucleic acid sequence encoding one of the two polypeptides, in particular chains, constituting the receptor.

Typically, when the receptor is a TCR, the barcoded primers specific for a nucleic acid sequence encoding the TCR are two different barcoded primers, wherein one barcoded primer is specific for a nucleic acid sequence encoding the alpha T-cell receptor and a second barcoded primer is specific for a nucleic acid sequence encoding the beta T-cell receptor.

Alternatively, when the receptor is a TCR, the barcoded primers specific for a nucleic acid sequence encoding the TCR are two different barcoded primers, wherein one barcoded primer is specific for a nucleic acid sequence encoding the gamma T-cell receptor and a second barcoded primer is specific for a nucleic acid sequence encoding the delta T-cell receptor.

Typically, when the receptor is a BCR and/or an antibody (as defined above), the barcoded primers specific for a nucleic acid sequence encoding the BCR and/or the antibody (as defined above) are two different barcoded primers, wherein one barcoded primer is specific for a nucleic acid sequence encoding the λ or κ chain of the BCR and/or the antibody and a second barcoded primer is specific for a nucleic acid sequence encoding the γ, δ, ε, α, or μ chain of the BCR and/or the antibody.

In the context of the invention, "a nucleic acid sequence encoding" the ligand (or the ligand's tag) or the receptor (or the receptor's tag) can be any type of nucleic acid as defined in the section "Definition" above. It can in particular be a DNA molecule or an RNA molecule. In a particular embodiment, said nucleic acid sequence encoding the ligand (or the ligand's tag) or the receptor (or the receptor's tag) consists or comprises of the mRNA sequence encoding said ligand (or said ligand's tag) or said receptor (or said receptor's tag), of a fragment thereof or a complementary sequence thereof. In another particular embodiment, said nucleic acid sequence encoding the ligand (or the ligand's tag) or the receptor (or the receptor's tag) consists or comprises of the cDNA sequence encoding said ligand (or said ligand's tag) or said receptor (or said receptor's tag), or of a fragment thereof. In still another embodiment, said nucleic acid sequence encoding the ligand (or the ligand's tag) or the receptor (or the receptor's tag) consists or comprised of the gene encoding said ligand (or said ligand's tag) or said receptor (or said receptor's tag), or of a fragment thereof.

As defined above, the barcode sequence or barcode set of sequences contained in a microreactor is distinguishable from the barcode sequence or barcode set of sequences contained in other microreactors, but the barcoded primers specific for the ligand (or ligand's tag)-encoding nucleic acid sequence and for the receptor (or receptor's tag)-encoding nucleic acid sequence contained in a given microreactor carry a common barcode sequence or barcode set of sequences. In other words, each microreactor comprises a unique type of barcode sequence or barcode set of sequences, optionally comprised in several barcoded primers, preferably in association with different primer sequences, while a particular barcode sequence or barcode set of sequences is preferably never included in two different microreactors.

In some embodiments, said barcoded primers are delivered on particles. In particular, in a preferred embodiment, said barcoded primers are initially bound to a particle. Indeed, binding said barcoded primers initially to a particle facilitates the delivery of only one type of barcoded primer into each microreactor.

As used herein, the terms "particle" and "bead" are used interchangeably.

The "particle" in context of the present invention refers to a microparticle.

In one embodiment the particle is a hydrogel particle, a polymeric particle or a magnetic particle.

The particle may have irregular or regular shape. For example, the particle can be spherical, ellipsoidal, or cubic.

"Hydrogel particles" are for example described in the International Patent Application No. WO 2008/109176, entitled "Assay and other reactions involving droplets". Examples of hydrogels include, but are not limited to agarose, poly(ethylene glycol) diacrylate, or acrylamide-based gels, such as bis-acrylamide, polyacrylamide, streptavidine acrylamide, poly-N-isopropylacrylamide, or poly N-isopropylpolyacrylamide or mixtures thereof. In one example the hydrogel particle comprises acrylamide, bis-acrylamide and strepatvidine acrylamide.

For example, an aqueous solution of a monomer may be dispersed in a microreactor, for instance a droplet, and then polymerized, e.g., to form a gel. Another example is a hydrogel, such as alginic acid that can be gelled by the addition of calcium ions. In some cases, gelation initiators (ammonium persulfate and TEMED for acrylamide, or $Ca^{2+}$ for alginate) can be added to a microreactor, for instance a droplet, for example, by co-flow with the aqueous phase, by diffusion and/or co-flow through the oil phase, or by coalescence of two different drops, e.g., as discussed in U.S. patent application Ser. No. 11/360,845, filed Feb. 23, 2006, entitled "Electronic Control of Fluidic Species," by Link, et ah, published as U.S. Patent Application Publication No. 2007/000342 on Jan. 4, 2007; or in U.S. patent application Ser. No. 11/698,298, filed Jan. 24, 2007, entitled "Fluidic Droplet Coalescence," by Ahn, et al.

In another set of embodiments, the particles may comprise one or more polymers and are thus herein referred to as "polymeric particle". Exemplary polymers include, but are not limited to, polystyrene (PS), polycaprolactone (PCL), polyisoprene (PIP), poly(lactic acid), polyethylene, polypropylene, polyacrylonitrile, polyimide, polyamide, and/or mixtures and/or co-polymers of these and/or other polymers.

In addition, in some embodiments, the particles may be magnetic and are thus referred to as "magnetic particle", which could allow for the magnetic manipulation of the particles. For example, the particles may comprise iron or other magnetic materials. The particles could also be functionalized so that they could have other molecules attached, such as proteins, nucleic acids or small molecules.

In some embodiments, the particle may be fluorescent.

In some embodiments, the particle may be functionalized, in particular to facilitate its identification and/or its sorting, for example using histidine, Flag, HA, streptavidin, acrydite DNA or biotin.

In one embodiment, the particle comprises streptavidin. Streptavidin may be coupled to the surface of the particle defined herein above or be inside said particle.

In one embodiment the hydrogel particles have a size from 1 pL to 1000 pL, such as 1 pL to 500 pL, 1 pL to 400 pL, 1 pL to 400 pL, 1 pL to 300 pL, for example 5 pL to 300 pL, 5 pL to 250 pL, 5 pL to 200 pL, 10 pL to 250 pL, 10 pL to 200 pL, 20 pL to 150 pL, 30 pL to 100 pL, 40 pL to 90 pL, 50 pL to 60 pL preferably 60 pL to 100 pL.

It will be understood by the skilled in the art that binding the barcoded primers temporally to a particle permits to provide particles having a high amount of barcoded primers. Furthermore, binding the barcoded primers initially to the particle facilitates the introduction of barcoded primers into each microreactor, in particular into each droplet, wherein the barcoded primers have the same barcode sequence.

Accordingly, in one embodiment, the barcoded primer is covalently bonded or non-covalently bonded to the particle.

"Non-covalently bonded" herein refers, for example, to a streptavidin-biotin bond. Other non-covalent bonds are known to the skilled in the art, such as avidin biotin bonds or his tag and nickel bonds.

"Covalently bonded" herein refers for example to an amino bond or an acrydite phosphoramidite bond.

"Streptavidin" generally refers to a 52.8 kDa protein purified from the bacterium *Streptomyces avidinii*. Streptavidin homo-tetramers have an extraordinarily high affinity for biotin with a dissociation constant (Kd) on the order of =10-14 mol/L, the binding of biotin to streptavidin is one of the strongest non-covalent interactions known in nature.

In a preferred embodiment, the non-covalent bond is a streptavidin-biotin bond.

Streptavidin-Biotin bonds are known to the skilled in the art. Accordingly, in one embodiment the particle as herein defined comprises streptavidin. Accordingly, in the same embodiment, the barcoded primers, as herein defined comprise biotin. In other words, the barcoded primers are functionalized with biotin.

Independent of the type of bond used to link the barcoded primers to the particle, the barcoded primers may further comprise at least one linker sequence.

Accordingly, in a further embodiment, the barcoded primer further comprises at least one linker sequence, said linker sequence being preferably comprised at the 5' end. Accordingly, in one embodiment, the barcoded primer comprises from 5' to 3' a linker sequence, a barcode sequence and a primer sequence.

In one embodiment, the "linker sequence" is a sequence with which the barcoded primer is optionally bonded to the particle.

"Optionally bonded" herein refers to the possibility that once the barcoded primers bonded to the particle are loaded into the microreactor or the plurality of microreactors, the barcoded primers might be released from the particle, so that the microreactor comprises the particle and the barcoded primers, said barcoded primers being separated from said particle.

Preferably, the linker sequence is a cleavable linker sequence, e.g., that can be cleaved upon application of a suitable stimulus, such as enzymatic and/or photocleavage.

"Cleavable linkers" are well known to the skilled in the art and are further described in Leriche et al. (2012) *Bioorg. Med. Chem.* 20:571-582. They may include, but are not limited to, TEV, trypsin, thrombin, cathepsin B, cathespin D, cathepsin K, caspase lumatrix metalloproteinase sequences, phosphodiester, phospholipid, ester, galactose, dialkyl dialkoxysilane, cyanoethyl group, sulfone, ethylene glycolyl disuccinate, 2-N-acyl nitrobenzenesulfonamide, a-thiophenylester, unsaturated vinyl sulfide, sulfonamide after activation, malondialdehyde (MDA)-indole derivative, levulinoyl ester, hydrazone, acylhydrazone, alkyl thioester, disulfide bridges, azo compounds, 2-Nitrobenzyl derivatives, phenacyl ester, 8-quinolinyl benzenesulfonate, coumarin, phosphotriester, bis-arylhydrazone, bimane bi-thiopropionic acid derivative, paramethoxybenzyl derivative, tert-butylcarbamate analogue, dialkyl or diaryl dialkoxysilane, orthoester, acetal, aconityl, hydrazone, b-thiopropionate, phosphoramidate, imine, trityl, vinyl ether, polyketal, alkyl 2-(diphenylphosphino)benzoate derivatives, allyl ester, 8-hydroxyquinoline ester, picolinate ester, vicinal diols, and selenium compounds. Cleavage conditions and reagents include, but are not limited to, enzymes, nucleophilic/basic reagents, reducing agents, photo-irradiation, electrophilic/acidic reagents, organometallic and metal reagents, and oxidizing reagents.

In a preferred embodiment, the cleavable linker is a photocleavable moiety, for example a photolabile chemical group followed a chain of 1 to 30 carbon atoms, typically a chain of 6 to 10 carbon atoms.

In a further preferred embodiment, the cleavable linker is a double-stranded DNA molecule containing a target site for a specific restriction endonuclease.

In a particular embodiment, the barcoded primers bound to a particle are released from the particle in the microreactor, in particular prior or after lysing the cells, as disclosed below.

The release of at least some of the barcoded primers may further occur after lysing the cells and before reverse transcribing the released nucleic acids hybridized to said barcoded primers or after lysing the cells and after reverse transcribing the released nucleic acids hybridized to said barcoded primers.

The skilled in the art will understand that depending on the time point selected for releasing the barcoded primers, the term "at least some of the barcoded primers" might refer to, for example, at least some of the barcoded primers hybridized to the nucleic acids released by the cells or a DNA/RNA duplex.

In one embodiment, the at least some of the barcoded primers can be released using any means, such as enzymes, nucleophilic/basic reagents, reducing agents, photo-irradiation, electrophilic/acidic reagents, organometallic and metal reagents, and oxidizing reagents.

In one embodiment, the at least some of the barcoded primers can be released using enzymatic and/or photocleavage. For example, an endonuclease may be used to cleave a linker sequence or any other sequence to release the at least some of the barcoded primers from the particle.

In a further embodiment, releasing the barcoded primer refers to disrupting the bond, such as a streptavidin biotin. Methods to disrupt a streptavidin biotin bond are known to the skilled in the art and include enzymatic digestion of streptavidin and/or denaturation of streptavidin.

In one embodiment, the barcoded primer is released by enzymatic digestion of streptavidin.

Preferably, each particle carries a barcode sequence or barcode set of sequences distinguishable from barcode sequences or barcode sets of sequences carried by other beads. In other words, each particle carries a unique majority type of barcode sequence or barcode set of sequences, optionally comprised in several barcoded primers, preferably at least some being in association with different primer sequences, while two different particles preferably do not carry the same majority barcode sequence or barcode set of sequences.

In a preferred embodiment, each microreactor contains a single particle carrying barcoded primers or less than 10 particles, in particular less than 9, 8, 7, 6, 5, 4, 3 or 2 particles carrying barcoded primers. In a particularly preferred embodiment, each microreactor carries a single particle carrying barcoded primers.

The "reverse transcriptase (RT)" in context of the present invention is an enzyme used to generate complementary DNA (cDNA) from an RNA template, in a process termed reverse transcription.

In one embodiment, the reverse transcriptase is selected from the group consisting of Superscriptase I, Superscriptase II, Superscriptase III, Superscriptase IV, Murine Leukemia RT, SmartScribe RT, Maxima H RT or Multi-Scribe RT.

In one embodiment, the reverse transcriptase is at a concentration of 1 to 50 U/μL, preferably 5 to 25 U/μL, for example at 12.5 U/μL.

In the context of the present invention, the "cell lysis buffer" is a composition enabling cell lysis, preferably without disruption of the microreactors, in particular of the droplets.

Preferably, the cell lysis buffer is compatible with RT activity and/or with reagents used for the recognition assay.

In one embodiment, the lysis buffer comprises enzymes selected from the group consisting of lysozyme, lysostaphin, zymolase, mutanolysin, glycanases, proteases, and mannose.

In one preferred embodiment, the lysis buffer comprises magnesium chloride, a detergent, a buffered solution and an RNase inhibitor.

In one embodiment, the magnesium chloride is used at a concentration of between 1 mM to 20 mM.

In one embodiment, the detergent is selected from the group consisting of Triton-X-100, NP-40, Nonidet P40, and Tween-20 and IGEPAL CA 630.

In one embodiment, the detergent is at a concentration of 0.1% to 10%.

Non-limiting examples of the buffered solution include Tris-HCl, Hepes-KOH, Pipes-NaOH, maleic acid, phosphoric acid, citric acid, malic acid, formic acid, lactic acid, succinic acid, acetic acid, pivalic (trimethylacetic) acid, pyridine, piperazine, picolinic acid, L-histidine, MES, Bistris, bis-tris propane, ADA, ACES, MOPSO, PIPES, imidazole, MOPS, BES, TES, HEPES, DIPSO, TAPSO, TEA (triethanolamine), N-Ethylmorpholine, POPSO, EPPS, HEPPS, HEPPSO, Tris, tricine, Glycylglycine, bicine, TAPS, morpholine, N-Methyldiethanolamine, AMPD (2-amino-2-methyl-1,3-propanediol), Diethanolamine, AMPSO, boric acid, CHES, glycine, CAPSO, ethanolamine, AMP (2-amino-2-methyl-1-propanol), piperazine, CAPS, 1, 3-Diaminopropane, CABS, or piperidine (see also, reachdevices.com).

Non-limiting examples of RNase inhibitors include RNase OUT, IN, SuperIN Rnase, and those inhibitors targeting a wide range of RNAse (e.g., A, B, C, 1 and T1).

In one example the lysis buffer is typically 0.36% Igepal CA 630, 50 mM Tris-HCl PH 8.

In a particular embodiment, said additional reagents are added into the microreactor, in particular into the microfluidic droplet, by injection from a reservoir, for example using electrical forces (picoinjection) (Abate et al. (2010) *Proc. Nat. Acad. Sci.* USA 107:19163-19166).

In another particular embodiment, said additional reagents are added into the microreactor, in particular into the microfluidic droplet, by coalescence with a second microreactor, in particular a second microfluidic droplet, comprising said additional reagents but not comprising any ligand or receptor. Droplets can be coalesced by a variety of methods known to the skilled person, including passive droplet coalescence (see Mazutis et al. (2009) *Lab on a Chip,* 9 (18): 2665-2672; Mazutis et al. (2012) *Lab Chip,* 12:1800-1806), droplet coalescence driven by local heating from a focused laser (Baroud et al. (2007) *Lab Chip* 7:1029-1033) or using electric forces (Chabert et al. (2005) *Electrophoresis* 26:3706-3715; Ahn et al. (2006) *Appl. Phys. Lett.,* 88:264105; Link et al. (2006) *Angew. Chem., Int. Ed.,* 45:2556-2560; Priest et al. (2006) *Appl. Phys. Lett.* 89:134101) or using magnetophoretic forces or using pneumatic controllers (see Xi et al. (2017) *Lab Chip* 17:751-771).

Said second microreactor, in particular said second microfluidic droplet, can be prepared by the same techniques as those disclosed above for the microreactors comprising the ligands and receptors.

By "coalescence" is meant herein the process by which two or more droplets or particles merge during contact to form a single daughter droplet or particle.

Preferably, said additional reagents are selectively added to positive microreactors, in particular after the separation step of the positive microreactors from the negative microreactors.

In a particular embodiment, in each microreactor, in particular in each positive microreactor, in which the above additional reagents are added, barcoded cDNAs are prepared by:

lysing the cells expressing or displaying receptors and the cells expressing or displaying ligands, to release mRNA from the cells, hybridizing at least some of the released mRNA coding for the receptor (or for the receptor's tag) to the receptor (or the receptor's tag)-encoding nucleic acid sequence specific primer, being optionally barcoded, and at least some of the released mRNA coding for the ligand (or for the ligand's tag) to the ligand (or the ligand's tag)-encoding nucleic acid sequence specific barcoded primer, in at least some of the microreactors, and reverse transcribing the released mRNA hybridized to the primers, being optionally barcoded thereby obtaining barcoded cDNAs.

As will be understood by the skilled person, when the ligand's tag or the receptor's tag is a barcode sequence, it is not necessary to prepare barcoded cDNAs as detailed above, since the nt sequences of the ligand or the receptor allow themselves their own identification.

"Barcoding" herein refers to adding a genetic sequence, a so-called barcode sequence as further defined herein above, to a nucleic acid which allows to distinguish said barcoded nucleic acid from a nucleic acid having another added genetic sequence, i.e. another unique barcode sequence.

The "cell lysis" in context of the present invention may be accomplished by enzymatic, physical, and/or chemical means, or any combination thereof, in particular enzymatic, physical, and/or chemical means. Other cell disruption methods may be also be used.

Accordingly, in one embodiment, the cells are lysed using enzymatic, physical, and/or chemical cell lysis.

"Enzymatic methods" to remove cell walls is well-established in the art. The enzymes are generally commercially available and, in most cases, were originally isolated from biological sources. Enzymes commonly used include lysozyme, lysostaphin, zymolase, mutanolysin, glycanases, proteases, and mannose.

As known by the skilled in the art "chemical cell lysis" is achieved using chemicals such as detergents, which disrupt the lipid barrier surrounding cells by disrupting lipid-lipid, lipid-protein and protein-protein interactions. The ideal detergent for cell lysis depends on cell type and source. Nonionic and zwitterionic detergents are milder detergents. The Triton X series of nonionic detergents, the IGEPAL CA 630 nonionic detergent, and 3-[(3-Cholamidopropyl)dimethylammonio]-I-propanesulfonate (CHAPS), a zwitterionic detergent, are commonly used for these purposes. In contrast, ionic detergents are strong solubilizing agents and tend to denature proteins, thereby destroying protein activity and function. SDS, an ionic detergent that binds to and denatures proteins, is used extensively in the art to disrupt cells.

"Physical cell lysis" refers to the use of sonication, thermal shock (above 40° C., below 10° C.), electroporation, or laser-induced cavitation.

In one example the cells are lysed on ice.

In one preferred embodiment, the cell lysis does not disrupt or destroy the microreactors, in particular the droplets, in context of the invention.

The "hybridization" mentioned above herein refers to a phenomenon in which the primer sequence present in the barcoded primer anneals to a complementary nucleic acid sequence of the released nucleic acids. Accordingly, as known by the skilled in the art, the temperature to use depends on the primer sequence and/or the polymerase enzyme used.

The step of reverse transcription defined above refers to reverse transcribing the released nucleic acids hybridized to said barcoded primers using the primer sequence in at least some of the microreactors. Reverse transcription is performed using the reverse transcriptase (RT) comprised in at least some of the microreactors.

"Reverse Transcription" or "RT reaction" is a process in which single-stranded RNA is reverse transcribed into a single-stranded complementary DNA (cDNA) by using total cellular RNA or poly(A) RNA, a reverse transcriptase enzyme, a primer, dNTPs and an RNase inhibitor. It will be understood by the skilled in the art, that the product of the reverse transcription is a RNA/DNA duplex comprising a single strand cDNA hybridized to its template RNA. As it will be further understood, said RNA/DNA duplex is further linked to the barcoded primer comprising the primer sequence used for the reverse transcription.

"Template switching" refers to a technology described originally in 2001, frequently referred to as "SMART" (switching mechanism at the 5' end of the RNA transcript) technology (Takara Bio USA, Inc). This technology has shown promise in generating full-length cDNA libraries, even from single-cell-derived RNA samples (Zhu et al.

(2001) Biotechniques 30:892-897). This strategy relies on the intrinsic properties of Moloney murine leukemia virus (MMLV) reverse transcriptase and the use of a unique template switching oligonucleotide (TS oligo, or TSO). During first-strand synthesis, upon reaching the 5' end of the RNA template, the terminal transferase activity of the MMLV reverse transcriptase adds a few additional nucleotides (mostly deoxycytidine) to the 3' end of the newly synthesized cDNA strand. These bases function as a TS oligo-anchoring site. Upon base pairing between the TS oligo and the appended deoxycytidine stretch, the reverse transcriptase "switches" template strands, from cellular RNA to the TS oligo, and continues replication to the 5' end of the TS oligo. By doing so, the resulting cDNA contains the complete 5' end of the transcript, and universal sequences of choice are added to the reverse transcription product. Along with tagging of the cDNA 3' end by oligo dT primers, this approach makes it possible to efficiently amplify the entire full-length transcript pool in a completely sequence-independent manner (Shapiro et al. (2013) *Nat. Rev. Genet.* 14:618-630).

Accordingly, it will be understood by the skilled in the art, that after reverse transcribing the nucleic acids, the microreactor further comprises cDNAs.

Accordingly, in one embodiment, at least some of the microreactors further comprise cDNAs produced by reverse transcription of nucleic acids from the cells contained in said microreactors.

In one embodiment, said cDNA refers to a single-stranded complementary DNA.

In a further embodiment, said cDNA is comprised in a RNA/DNA duplex.

In one embodiment, the RNA/DNA duplex refers to the RNA that has been reverse transcribed and is hybridized to the primer sequence of at least one of the primers, which is optionally barcoded, contained in the microreactor.

As it will be understood by the skilled in the art, in one embodiment, the RNA/DNA duplex is linked to the primer, which is optionally barcoded, comprising the primer sequence to which the nucleic acid, preferably mRNA, was hybridized and which was used for reverse transcription.

In one example, hybridization and reverse transcription are performed by incubating the microreactors for example for 1 h or 2 h at 55° C. or 50° C. during typically mixing of the microreactors at for example 550 rpm.

Identification of Ligand Species and Receptor Species

Identification of the ligand species and the receptor species contained in each microreactor, in particular each positive microreactor, can be carried out by any technique well-known from the skilled person. In particular, identification of the ligand species and the receptor species contained in each microreactor, in particular each positive microreactor, can be carried out by sequencing, in particular by sequencing DNA, the barcoded cDNAs obtained as detailed above, or the tags.

In one embodiment, the barcoded cDNAs produced by the reverse transcription as defined above are recovered and further used for identification, typically, by subsequent amplification and sequencing library preparation.

Accordingly, in one embodiment, the method of the invention further comprises recovering cell cDNAs produced by reverse transcription in at least some of the microreactors, preferably in the positive microreactors.

"Recovering" herein refers to isolating the barcoded cDNAs produced by reverse transcription in at least some of the microreactors from said plurality of microreactors.

In one embodiment, recovering herein refers to collecting the microreactors comprising barcoded cDNA produced by reverse transcription or collecting the aqueous composition contained in said microreactors comprising said barcoded cDNA, and separating the barcoded cDNA comprised in the aqueous composition.

In one particular embodiment, recovering herein refers to collecting the microfluidic droplets comprising barcoded cDNA produced by reverse transcription, breaking the microfluidic droplets and separating the barcoded cDNA comprised in the aqueous composition from the oil phase of said microfluidic droplets.

Methods to isolate nucleic acids, in particular cDNA from microfluidic droplets are known to the skilled in the art and comprise for example, collecting the microfluidic droplets and breaking the emulsion by, for example, applying an electrical field (electrocoalescence) or by adding a chemical emulsion breaking agent, such as perfluoro-octanol in the case of droplets in fluorinated carrier oils. In one example, the broken emulsion is typically centrifuged for, for example, 10 min at 10 000 g at 4° C. and the supernatant comprising the barcoded cDNA in the aqueous phase is recovered.

In one embodiment, the method further comprises the step of removing unincorporated barcoded primers from the aqueous composition of the microreactors. In one preferred embodiment, the step of removing unincorporated barcoded primers from the aqueous composition of at least some of the microreactors takes place after the step of recovering the barcoded cDNA produced by reverse transcription as defined herein above.

Preferably, the step of removing unincorporated barcoded primers precedes the amplification step and/or the sequencing step defined herein below.

In one embodiment, removing unincorporated barcoded primers comprises contacting the aqueous composition of the at least some of the microreactors with a purification substrate wherein the purification substrate removes unincorporated barcoded primers. In one embodiment, the purification substrate comprises beads or particles, which, optionally, form a column. In a further example, unincorporated barcoded primers are removed by size selection using for example an acrylamide or an agarose gel.

In one embodiment, the step of removing unincorporated barcoded primers comprises contacting the aqueous composition of the at least some of the microreactors with an exonuclease, such as the exonuclease Exo1, to degrade the unincorporated barcoded primers within the aqueous composition of the at least some of the microreactors.

In certain embodiments of this step, the exonuclease degrades single stranded nucleic acid sequences from the aqueous compositions comprising the cDNA.

It will be understood by the skilled in the art, that the barcoded cDNA obtained after reverse transcription is typically present in form of a RNA/DNA complex and thus protected from said exonucleases.

In one embodiment, the barcoded cDNA comprises one or more modified nucleotides or nucleotide analogs, for example for facilitating purification of the barcoded cDNA sequences or molecules.

For example, the nucleotides may be employed as phosphorothioate derivatives (replacement of a non-bridging phosphoryl oxygen atom with a sulfur atom) which have increased resistance to nuclease digestion. 2'-methoxyethyl (MOE) modification (such as the modified backbone commercialized by ISIS Pharmaceuticals) is also effective.

Other examples of modified nucleotides include derivatives of nucleotides with substitutions at the 2' position of the sugar, in particular with the following chemical modifications: O-methyl group (2'-O-Me) substitution, 2-methoxyethyl group (2'-O-MOE) substitution, fluoro group (2'-fluoro) substitution, chloro group (2'-Cl) substitution, bromo group (2'-Br) substitution, cyanide group (2'-CN) substitution, trifluoromethyl group (2'-CF$_3$) substitution, OCF$_3$ group (2'-OCF$_3$) substitution, OCN group (2'-OCN) substitution, O-alkyl group (2'-O-alkyl) substitution, S-alkyl group (2'-S-alkyl) substitution, N-alkyl group (2'-N-akyl) substitution, O-alkenyl group (2'-O-alkenyl) substitution, S-alkenyl group (2'-S-alkenyl) substitution, N-alkenyl group (2'-N-alkenyl) substitution, SOCH$_3$ group (2'-SOCH$_3$) substitution, SO$_2$CH$_3$ group (2'-SO$_2$CH$_3$) substitution, ONO group (2'-ONO$_2$) substitution, NO$_2$ group (2'-NO$_2$) substitution, N$_3$ group (2'-N$_3$) substitution and/or NH$_2$ group (2'-NH$_2$) substitution. Other examples of modified nucleotides include biotin labeled nucleotides.

Other examples of modified nucleotides include nucleotides wherein the ribose moiety is used to produce locked nucleic acid (LNA), in which a covalent bridge is formed between the 2' oxygen and the 4' carbon of the ribose, fixing it in the 3'-endo configuration.

Other examples of nucleotide analogs include deoxyinosine.

Other examples of nucleotide analogs include Biotinylated, fluorescently labelled nucleotide . . . .

For example, Biotin-11-dCTP can be used as a substrate for the reverse transcriptase to incorporate biotins into the cDNA during polymerization, allowing affinity purification using streptavidin or avidin.

In one embodiment, the barcoded cDNA is further treated with RNAse A and/or RNAse H.

"RNAse A" is an endoribonuclease that specifically degrades single-stranded RNA at C and U residues.

In one embodiment, the RNAse A is at a concentration of 10 to 1000 μg/μL, preferably 50 to 200 μg/μL, for example at 100 μg/μL.

"RNAse H" is a family of non-specific endonucleases that catalyze the cleavage of RNA via a hydrolytic mechanism. RNase H ribonuclease activity cleaves the 3'-O—P bond of RNA in a DNA/RNA duplex substrate to produce 3'-hydroxyl and 5'-phosphate terminated products.

In one embodiment, the RNAse H is at a concentration of 10 to 1000 μg/μL, preferably 50 to 200 μg/μL, for example at 100 μg/μL.

In one embodiment, the barcoded cDNA is further treated with Proteinase K.

"Proteinase K" is a broad-spectrum serine protease and digests proteins, preferentially after hydrophobic amino acids.

In one embodiment, the Proteinase K is at a concentration of 0.1 to 5 mg/mL, preferably 0.1 to 1 mg/mL, for example at 0.8 mg/mL.

In one embodiment, the barcoded cDNAs obtained after reverse transcription are sequenced to allow identification of receptors and ligands contained in the same microreactor.

In one embodiment, the step of sequencing the barcoded cDNA may comprise performing a next generation sequencing (NGS) protocol on a sequencing library. Any type of NGS protocol can be used such as the MiSeq Systems (Illumina®), the HiSeq Systems (Illumina®), the NextSeq System (Illumina®), the NovaSeq Systems (Illumina®), the IonTorrent system (ThermoFisher), the IonProton system (ThermoFisher), or the sequencing systems such as Pacific Biosciences™ sequencing system and Nanopore™ sequencing system.

In certain embodiments, the NGS protocol comprises loading an amount of the sequencing library between 1 PM and 20 pM, in particular between 1.5 PM and 20 pM, per flow cell of a reagent kit.

In one embodiment, the NGS sequencing protocol further comprises the step of adding 5-60% PhiX to the amount of the sequencing library or to the flow cell of the reagent kit.

In one embodiment, prior to sequencing, the barcoded cDNAs are further amplified.

In one embodiment, the amplification step is performed by a polymerase chain reaction (PCR), and/or a linear amplification.

In one embodiment, the linear amplification precedes the PCR reaction.

In one embodiment, the linear amplification is an in vitro transcription.

In one embodiment, the linear amplification is an isothermal amplification.

In one embodiment, said amplification step is performed after removing unincorporated barcoded primers. In one embodiment, said amplification step is performed prior to the sequencing step defined herein above.

In one embodiment, the barcoded cDNA produced after reverse transcription is quantified using qPCR.

In one embodiment, specific sequences necessary for sequencing are added during amplification or by ligation of adaptors, thereby generating a sequencing library.

As will be understood by the skilled person, since the barcoded cDNAs from a particular microreactor carry a same specific majority barcode sequence or barcode set of sequences which is different from the majority barcode sequences or barcode sets of sequences included in other microreactors, it is possible to determine which identified ligand species were contained in the same microreactor, in particular in positive microreactors, as a particular identified ligand receptor.

Establishing a Subset of Positive Microreactors Containing the Same Receptor Species By "establishing a subset" is meant herein forming either physically or intellectually a subset of said positive microreactors.

By "same receptor species" is meant herein receptor species comprising or consisting of the same sequence (taking into account the optional few errors induced by reverse transcription, amplification and/or sequencing).

Establishing a subset of positive microreactors containing the same receptor species can be carried out by any suitable technique, in particular by comparison of the sequences of the receptor species identified in the identification step above.

Probability Determination and Identification of the Cognate Pair

In a particular embodiment, the probability that in a given subset of positive microreactors containing the same receptor species, the ligand species recognized by the receptor species corresponds to the most frequent co-compartmentalized ligand species, is determined in function of the diversity of ligand species, the average number of true positive microreactors for the given subset of positive microreactors containing the same receptor species and the average number of each non-cognate ligand species contained in positive microreactors containing the same receptor species.

In that embodiment, the average number of true positive microreactors for a given subset of positive microreactors containing the same receptor species, is preferably determined according to the following expression:

$$l = fn,$$

where:

l is the average number of true positive microreactors in the given subset of positive microreactors containing the same receptor species;

n is the number of microreactors containing said receptor species; and f is the average frequency of each ligand species per microreactor which is determined as the ratio between a number of ligand species per microreactor and the total diversity of ligands species.

Still preferably, the average number of each non-cognate ligand species contained in positive microreactors containing the same receptor species, is determined according to the following expression:

$$b = f(l+e),$$

where:

b is the average number of each non-cognate ligand species contained in positive microreactors containing the same receptor species; and e is an average number of measurement errors within the given subset of positive microreactors which is determined as product of a rate of technical false positives due to the assay and the number of microreactors containing said receptor species.

In a particular embodiment, said probability for a given subset of microreactors is determined according to the following expression:

$$\sigma = \sum_{k=1}^{+\infty} \left( \frac{\int_b^{+\infty} t^{k-1} e^{-t} dt}{(k-1)!} \right)^{d-1} e^{-l} \frac{l^k}{k!},$$

where:

σ is said probability for the given subset of positive microreactors containing the same receptor species;

d is the diversity of ligand species;

l is the average number of true positive microreactors in the given subset of positive microreactors containing the same receptor; and b is the average number of each non-cognate ligand species contained in positive microreactors containing the same receptor species.

For each identified receptor species, its cognate ligand species can therefore be identified as the most frequently co-compartmentalized ligand species, with probability σ to be a true positive cognate pair.

Analyzing System

The present invention also concerns an analyzing system implementing the method of identification as explained above.

According to one embodiment of the invention, the analyzing system comprises a data base, co-compartmentalizing means, assaying means, identifying means, determining means and comparing means.

The data base is for example a computer memory able to stock computer files comprising a set of ligands and a set of receptors. Each of these sets is acquired using appropriate assays or tests.

Advantageously, this memory is able to stock several redundant sets of ligands and several redundant sets of receptors in order to improve the precision of the method.

The co-compartmentalizing means present appropriate means able to co-compartmentalise ligand species and receptor species to form a set of microreactors, so as each microreactor comprises at least one ligand species and preferably at least one receptor species.

The assaying means present appropriate means able to assay the recognition between ligands and receptors in each microreactor and based on this assay, classify each microreactor as positive or negative.

The identifying means present appropriate means able to identify ligand species and receptor species contained in each positive microreactor.

The determining means present appropriate means able to determine the probability that in a given subset of positive microreactors containing the same receptor species, the ligand species recognizing the receptor species corresponds to the most frequent co-compartmentalized ligand species.

The comparing means present appropriate means able to compare the determined probability with a predetermined threshold and if this probability is greater than the predetermined threshold, identify as a cognate pair the receptor species and the most frequent co-compartmentalized ligand species.

According to one embodiment of the invention, the determining means and the comparing means are formed by a computer. The computer comprises a processer and a memory able to stock a plurality of programs. These programs are executed by the processor and able to determine said probability and compare it with the predetermined threshold according to methods known in the art.

Medical Uses

The present invention also concerns the use of a composition comprising (i) an isolated antigen identified by the method of identification according to the invention as being part of a TCR/antigen pair, and/or (ii) an isolated T cell expressing a TCR identified by the method of identification according to the invention as being part of a TCR/antigen pair, and/or (iii) an isolated TCR identified by the method of identification according to the invention as being part of a TCR/antigen pair and/or (iv) an ex-vivo engineered immune cell expressing either the antigen and/or the TCR identified by the method of identification according to the invention as being part of a TCR/antigen pair, for the manufacture of a medicament intended for the prevention and/or treatment of cancer, autoimmune disease, inflammatory and autoimmune disease, infectious disease, or metabolic disease.

The present invention also concerns a method, in particular an in vitro method, for diagnosing cancer, autoimmune disease, inflammatory and autoimmune disease, infectious disease, or metabolic disease, wherein said method comprises the use of (i) an isolated antigen identified by the method of identification according to the invention as being part of a TCR/antigen pair, and/or (ii) an isolated T cell expressing a TCR identified by the method of identification according to the invention as being part of a TCR/antigen pair.

The present invention also concerns a method for predicting the response of a patient to a therapy for treating cancer, autoimmune disease, inflammatory and autoimmune disease, infectious disease, or metabolic disease, wherein said method comprises the use of (i) an isolated antigen identified by the method of identification according to the invention as being part of a TCR/antigen pair, and/or (ii) an isolated T cell expressing a TCR identified by the method of identification according to the invention as being part of a TCR/antigen pair.

Another object of the invention concerns a method of prevention and/or treatment of cancer, autoimmune disease, inflammatory and autoimmune disease, infectious disease, or metabolic disease, comprising administering, in a subject in need thereof, a therapeutically efficient amount of a composition comprising (i) an isolated antigen identified by the method of identification according to the invention as being part of a TCR/antigen pair, and/or (ii) an isolated T cell expressing a TCR identified by the method of identification according to the invention as being part of a TCR/antigen pair, and/or an antigen identified by the method of identification according to the invention presented by a autologous dendritic cells or an ex vivo engineered dendritic cells and/or (iii) an isolated TCR identified by the method of identification according to the invention as being part of a TCR/antigen pair and/or (iv) an ex-vivo engineered immune cell expressing either the antigen and/or the TCR identified by the method of identification according to the invention as being part of a TCR/antigen pair.

Throughout the instant application, the term "and/or" is a grammatical conjunction that is to be interpreted as encompassing that one or more of the cases it connects may occur.

As used in this specification and the appended claims, the singular forms "a," "an" and "the" include plural references, such as a plurality of the object referred to, unless the content clearly dictates otherwise.

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

In the entire description, features described in one section are entirely applicable to other sections of the instant description, unless specified. For instance, the description referring to "barcoded primers" as given in the section "Definition" is entirely applicable to the section called "Method of identification".

The present invention will be further disclosed by examples below.

EXAMPLES

Figure 1:
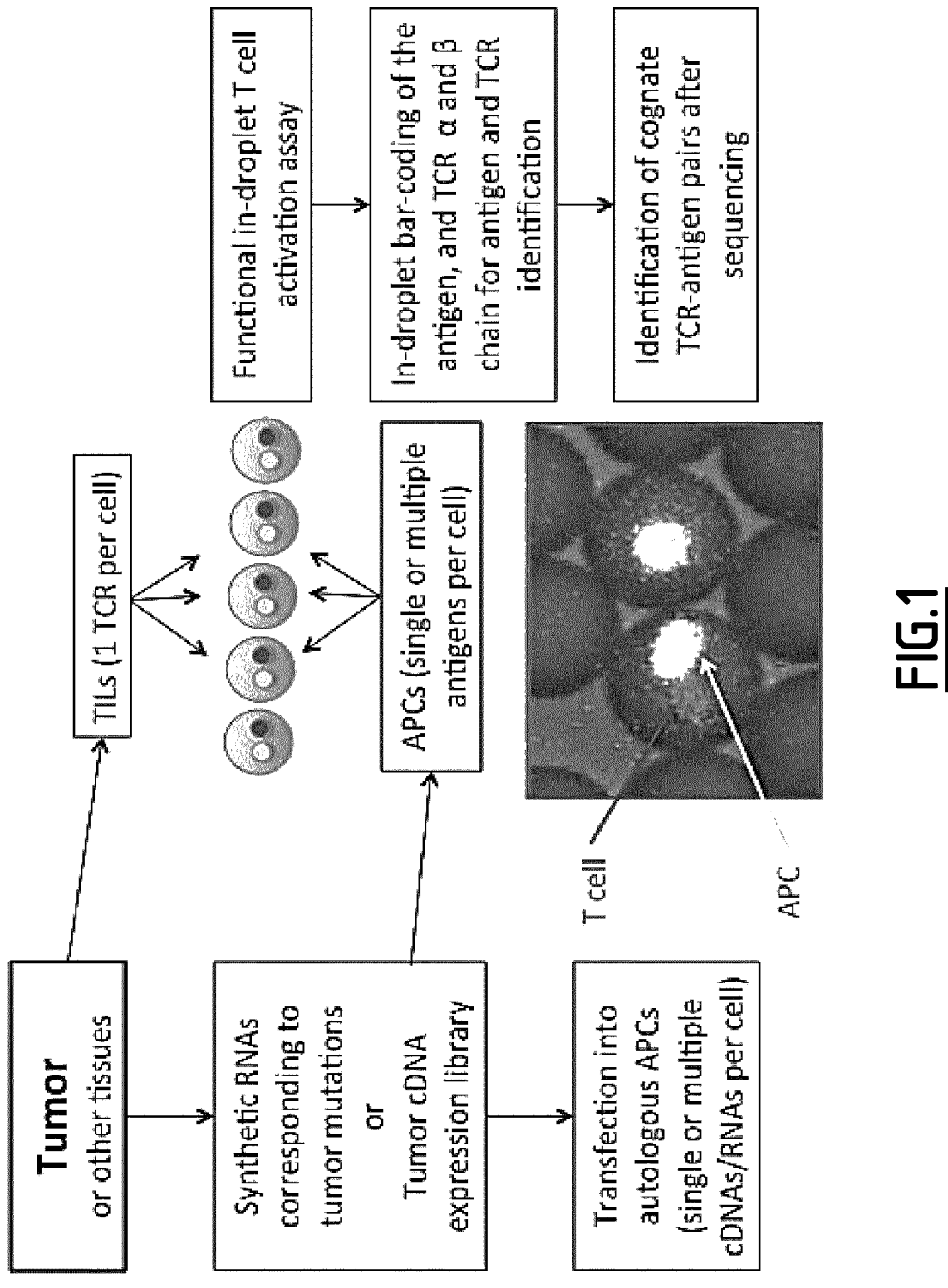
FIG. 1: Example of workflow

Multiple variations for identifying cognate antigen/receptor pairs are possible and are described in table 1.

Table 1 shows examples of strategies for linking antigen and TCR sequence recovery. The table exemplify the source of material, the method (if any) for mRNA isolation from tissue, the method for generating antigen cDNA (if any), the method of cDNA normalization (if any), the source of APC, the method for antigen expression, the method for antigen barcoding, the method for inducting antigen expression by APC, the methods for T cells and APC co-encapsulations, the methods for detecting T cells activation, the methods for enriching positive hits, the method for barcoding TCR and/or antigen and/or gene of interest, the method for recovering cDNA, the method for amplifying cDNA, the methods for sequencing.

TABLE 1 variations for identifying cognate antigen/receptor pairs

| Steps / Tissue | Solid tumor | Liquid tumor | Circulating tumor cells | Circulating tumor DNA | Options — Draining lymph nodes | Ascites | Other effusion | Normal sample for library normalization | Class I and/or II expression sample |
|---|---|---|---|---|---|---|---|---|---|
| Isolation mRNA | RNA extraction | | | | | | | | |
| Reverse transcription | Total mRNA | Specific mRNA | None (RT from cell lysate) Identification of potential genes encoding T cell antigens by using sequencing to determine the genome, exome or transcriptome of a tumor none | None (no RT) | Template switch for full length cDNA | Incl. UMI for molecular count | None (DNA sequencing) | | |
| Normalization | Equalization of all cDNA species using duplex specific nuclease | | | | | | | | |
| APC | Artificial (beads of any type) | Engineered (K562, immortalized cells . . . ) | EBV transformed autologous B cells | Primary APC | | Barcoded tetramer or multimer | | | |
| Antigen expression system | Minigenes in vectors | Multiple vectors | Split pool synthesis mediated vector construction (with bead support +/− release of beads at the end of the process) | | Transcribed RNA from examples above | Synthetic RNA | | Number antigens per APC: from 1 to 50 genes, ideally 25 | Antigen length (from 20 nt to 100 nt) |
| Antigen barcoding | Barcode per antigen (i.e. tag from 1 nt to several nt) | Barcode per combination of antigen | None (antigen sequence sequenced in part of fully) | | None (case 1 antigen) | | | | |

TABLE 1-continued variations for identifying cognate antigen/receptor pairs

| Steps / Tissue | Solid tumor | Liquid tumor | Circulating tumor cells | Circulating tumor DNA | Draining lymph nodes | Ascites | Other effusion | Normal sample for library normalization | Class I and/or II expression sample |
|---|---|---|---|---|---|---|---|---|---|
| | | | | | Options | | | | |
| Transduction APC | Transfection in solution | Transduction in solution | Transfection in solution | Transfection in droplet | Transduction in droplet | | MOI of 0.1 to 1000 | Penetratin of synthetic DNA released in droplet from beads used for the split pool synthesis | |
| T cell/APC co encaps | Double Poisson statistic | Complex of T cells and APC pre formed before being encapsulated in droplet | 1 follow Poisson stat. the other do not | None of them follow Poisson distribution | | Droplet from 40 to 1 nL volume | | Fusion of 2 droplets | |
| Detection of activation | Secretion of cytokine (IFNg, TNFa) detection (beadline, cell surface) | Degranulation detection (perforin, granzyme) using fluorescent antibodies | Activation marker detection (CD137, CD69, HLA-DR, . . . ) using fluorescent antibodies | | None (based on sequencing: gene specific primer, whole transcriptome) | | | | |
| Enrichment of positive hits | Droplet sorting using acoustic wave | Droplet sorting using DEP | Magneto-phoresis | Pneumatic controllers | | None (use of sequencing readout) | | | |

TABLE 1-continued variations for identifying cognate antigen/receptor pairs

| Steps / Tissue | Options | | | | | | | | |
|---|---|---|---|---|---|---|---|---|---|
| | Solid tumor | Liquid tumor | Circulating tumor cells | Circulating tumor DNA | Draining lymph nodes | Ascites | Other effusion | Normal sample for library normalization | Class I and/or II expression sample |
| Barcoding | One to one electro-coalescence | Droplet fusion by alternating current (AC) field electro-coalescence in microchannels | | | Gene linkage (TCR and antigen barcode/ sequence) RT (+/-PCR) | Hydrogel beads CDNA synthesis (+/-PCR) | Solid beads CDNA synthesis (+/-PCR) | Hydrogel beads mRNA capture and cDNA synthesis out of droplet (+/-PCR) | Solid beads RNA capture and cDNA synthesis out of droplet (+/-PCR) |
| cDNA recovery | Emulsion breaking with PFO | Emulsion breaking with HFE/PFO | Emulsion breaking with electrocoaslescence | Coalescence | | | | | |
| Amplification | Nested PCR | PCR | Unbiased amplification (IVT) | | | | | | |
| Sequencing | Illumina TCR chains | PacBiO Gene panel | Ion torrent antigen | Nanopore Whole transcriptome | | | | | |
| Analysis | | | | | . . . | | | | |
| Pair recovery | See example 10 | | | | | | | | |

Below are specific examples.

Example 1 (Sorting and Sequencing)

Cognate pairs of tumor T cell antigens and T cell receptors are identified using the following method.

1. Isolation of T cells and tissue from patients (in particular from tumor tissue using protease and DNAase in $CO_2$ independent medium for 45 min at room temperature or 37° C., or from lymph-node, ascites or other effusions as well as blood), isolation of T cells and isolation of tissue cells expressing MHC class II and/or class I molecules.

2. Isolation of mRNA from the tissue and reverse transcription to produce cDNA. Addition of a sense and antisense universal primer sequence to allow the specific amplification of cDNA during subsequent RT and PCR—i.e. allowing specific recovery of cDNA encoding antigen in steps 8 and 9.

3. Equalisation of the concentrations of all cDNA species. The cDNA library is normalized using duplex-specific nuclease (DSN) (Zhulidov et al. (2004). *Nucleic Acids Res*. 32 (3): e37; Bogdanova et al. (2010). *Curr. Protoc. Mol. Biol*. Chapter 5: Unit 5.12.1-27.), using DSN (Evrogen) according to the manufacturer's instructions.

4. Preparation of EBV transformed autologous B cells

5. Transduction of the EBV transformed autologous B cells with the cDNA library (using for example a lentiviral system) at a multiplicity of infection (m.o.i.) of ~10-1000 to generate antigen-presenting cells (APCs) presenting multiple antigens. A selective marker or reporter gene is integrated into the lentiviral vector sequence in order to select/sort transduced APCs.

6. Co-compartmentalisation of 1-10 transfected B cells (APCs) with single T cells in aqueous droplets using a microfluidic system. The transfected B cells are mixed with the T cells in X-VIVO 15 (Lonza) and human serum so as to give an average 1 of 1-10 B cells and 0.1-1 T cells per droplet after compartmentalization in droplets. Droplets are created by hydrodynamic flow-focusing (Anna et al. (2003) *Applied Physics Letters,* 82 (3), 364-366) on a microfluidic device with a nozzle 25 μm wide, 40 μm deep, and 40 μm long (Eyer et al. *Nat Biotechnol* (2017)), fabricated using soft-lithography in poly-(dimethylsiloxane) (PDMS) (Duffy et al. (1998) *Anal. Chem., * 70:4974-4984) as described in Mazutis et al. (2013) *Nat. Protocols* 8:870-891. The continuous phase comprised 2% (w/w) 008-FluoroSurfactant (RAN Biotechnologies) in Novec HFE7500 (3M) fluorinated oil. The aqueous cell suspension and an aqueous solution comprising paramagnetic colloidal nanoparticles and other detection reagents (see below) are co-flowed on-chip. The flow rates (around 800 μl/h for oil, and 100 μl/h for each aqueous solution, supplied using a neMESYS syringe pump, Cetoni) are adjusted to create droplets of 40±3 pl.

7. Detection of T cell activation in the droplets and sorting of the droplets containing activated T cells. To detect T cells secreting TNF-α and IFN-γ a fluorescent sandwich immunoassay is used, in which secreted TNFα and/or IFN-γ are captured onto paramagnetic colloidal nanoparticles coated with anti-TNFα and/or IFN-γ capture antibodies in each droplet (Eyer et al. *Nat Biotechnol* (2017)). Upon application of a magnetic field, the ~1,300 nanoparticles in each droplet form an elongated aggregate (termed a beadline). Each droplet also contains anti-TNFα antibodies whose epitopes do not overlap with the capture reagent (red fluorescent) that relocates onto the beadline if TNFα is secreted and/or anti-IFN-γ antibodies whose epitopes do not overlap with the capture reagent (green fluorescent) that relocated to the beadline if IFN-γ is secreted. The distribution of fluorescence in the droplets is analyzed by re-injecting them into a second microfluidic chip, where each droplet is excited with superimposed laser lines (for example, 405 nm and/or 488 nm, and/or 561 nm, and/or 638 nm) and epifluorescence detected using photomultiplier tubes (PMTs). Secretion of TNFα and IFN-γ are determined from red- and green-fluorescence localization to the beadline, respectively. The bioassay readout is monitored and fluorescence activated dielectrophoretic sorting (Baret et al. (2009). *Lab Chip,* 9:1850-1858) of droplets containing activated T cells and co-compartmentalized B cells is controlled by dedicated software.

8. Addition of unique (droplet-specific) barcoded cDNA primers to each droplet by one-to-one electrocoalescence (Chabert et al. (2005). *Electrophoresis,* 26 (19), 3706-3715) with ~1 nL droplets containing single hydrogel beads (Abate et al. (2009). *Lab on a Chip,* 9 (18), 2628), cell lysis reagent and reverse transcription reagents, produced as described (Klein et al. (2015). *Cell,* 161 (5), 1187-1201; Zilionis et al. (2016). *Nature Protocols,* 12 (1), 44-73). Each bead carries multiple copies of cDNA primers able to prime cDNA synthesis on the mRNA encoding the antigens and mRNA encoding the TCR α and β chains, and primers on the same bead carry a bead-specific barcode. The beads are produced by split-and-pool synthesis as described (Klein et al. (2015). *Cell,* 161 (5), 1187-1201; Zilionis et al. (2016). *Nature Protocols,* 12 (1), 44-73). After droplet fusion, the cells are lysed, primers released from the hydrogel beads by UV-photocleavage and cDNA synthesis performed as described (Klein et al. (2015). *Cell,* 161 (5), 1187-1201; Zilionis et al. (2016). *Nature Protocols,* 12 (1), 44-73).

9. Breaking of the emulsion and pooling of the barcoded cDNAs (encoding for TCR and antigen). The emulsion containing the barcoded cDNA was broken by adding one volume of 1H, 1H,2H,2H-Perfluoro-1-octanol (370533, Sigma). The DNAs from each droplet all carry the same barcode. The barcoded cDNA are specifically amplified by a nested PCR approach using forward primers specific for the barcoded cDNA primers and backwards primers specific for each TCR α/β V gene, and the constant region flanking the antigens, as described in (Han et al. (2014). *Nature Biotechnology,* 32(7), 684-692) for TCR pairs recovery and gene amplification.

10. The barcoded cDNAs are sequenced with the Illumina system, using 2×150 bp paired-end reads for sequencing TCR α/β and recovering V(D)J sequences (i.e. capturing at least the CDR3 of both α and β sequences), and 2×50 bp paired-end reads for antigen identification.

11. Analysis of the sequencing data to identify the pools of antigens recognised by single TCR α and β chains from activated T cells. Bioinformatic data processing is used for sequence read trimming, merging, barcode extraction and clustering and sequence characterization and filtering. Antigen consensus reads passing threshold from B cells co-compartmentalized with activated T cells and the TCR α and β chain consensus reads passing threshold from the T cells carry the same barcode.

12. Identification of cognate antigen-TCR pairs as Example 10.

Example 2 (Sorting Only+ Barcoded cDNA)

Cognate pairs of tumor T cell antigens and T cell receptors are identified using the method described in Example 1 except that step 2 is replaced by the following step:

2. Isolation of mRNA from the tissue and reverse transcription using barcoded primers to produce cDNA and the allows subsequent identification of the cDNA by sequencing in steps 10 and 11. Addition of a sense and antisense universal sequence to allow the specific amplification of cDNA during subsequent RT and PCR—i.e. allowing specific recovery of cDNA encoding antigen in steps 8 and 9.

Example 3 (without Droplet Sorting)

Cognate pairs of tumor T cell antigens and T cell receptors are identified using the method described in examples 1 and 2 except that step 7 is deleted and steps and 8 are replaced by the following steps.

8. Addition of unique (droplet-specific) barcoded cDNA primers to each droplet by one-to-one electrocoalescence (Chabert et al. (2005). *Electrophoresis*, 26 (19), 3706-3715) with ~1 nL droplets containing single hydrogel beads (Abate et al. (2009). *Lab on a Chip*, 9 (18), 2628), cell lysis reagent and reverse transcription reagents, produced as described (Klein et al. (2015). *Cell*, 161 (5), 1187-1201; Zilionis et al. (2016). *Nature Protocols*, 12 (1), 44-73). Each bead carries multiple copies of cDNA primers able to prime cDNA synthesis on the mRNA encoding the antigens, on the mRNA encoding the TCR α and β chains and a on panel of mRNAs encoding activation markers (IFNg, TNFa, CD69, HLA-DR, CD137, GRZM, PRF, CD25, OX40, CD38), and primers on the same bead carry a bead-specific barcode. The beads are produced by split-and-pool synthesis as described (Klein et al. (2015). *Cell*, 161 (5), 1187-1201; Zilionis et al. (2016). *Nature Protocols*, 12 (1), 44-73). After droplet fusion, the cells are lysed, primers released from the hydrogel beads by UV-photocleavage and cDNA synthesis performed as described (Klein et al. (2015) *Cell*, 161 (5), 1187-1201; Zilionis et al. (2016). *Nature Protocols*, 12 (1), 44-73).

9. Breaking of the emulsion and pooling of the barcoded cDNAs (encoding for TCR, antigen and activation markers). The emulsion containing the barcoded cDNA was broken by adding one volume of 1H, 1H,2H,2H-Perfluoro-1-octanol (370533, Sigma). The DNAs from each droplet all carry the same barcode. The barcoded cDNA are specifically amplified by a nested PCR approach using forward primers specific for the barcoded cDNA primers and backwards primers specific for each TCR α/β V gene, and the constant region flanking the antigens, as described in Han et al. 2014 (NBT) for TCR pairs recovery and gene amplification.

10. The barcoded cDNAs are sequenced with the Illumina system, using 2×150 bp paired-end reads for sequencing TCR α/β and recovering V(D)J sequences (i.e. capturing at least the CDR3 of both α and β sequences), and 2×50 bp paired-end reads for antigen identification and sequencing of the activation marker mRNAs.

11. Analysis of the sequencing data to identify the pools of antigens recognised by single TCR α and β chains from activated T cells. Bioinformatic data processing is used for sequence read trimming, merging, barcode extraction and clustering and sequence characterization and filtering. Antigen consensus reads passing threshold from B cells co-compartmentalized with activated T cells and the TCR α and β chain consensus reads passing threshold and the activation marker reads from the T cells carry the same barcode.

Example 4: Sorting and Sequencing of the Activation Markers

Cognate pairs of tumor T cell antigens and T cell receptors are identified as in example 3, except that step 7 from examples 1 and 2 is not deleted.

Example 5 (Synthetic mRNA Coding for Identified Candidate Antigens)

Cognate pairs of tumor T cell antigens and T cell receptors are identified as in examples 1 to 4, except that steps 2 to 5 are replaced by the following steps.

2. Identification of potential genes encoding T cell antigens by using sequencing to determine the genome, exome or transcriptome of a tumor.

3. Transfection of antigen-presenting cells (APCs) with synthetic mRNAs (either as a tandem genes or as single gene) encoding antigens identified by sequencing at step 2. Synthetic RNA are generated by in vitro-transcription which are subsequently electroporated into APC/B cells (see Sahin et al. (2017) *Nature* 547: 222-226).

Synthetic RNA may optionally contain an 'antigen barcode' and/or a universal sequence to amplify the RNA to retrieve the antigen specific information during the functional readout (combining either phenotypic screening and sequencing or by sequencing only).

Example 6 (Split and Pool with the Individual mRNA)

Cognate pairs of tumor T cell antigens and T cell receptors are identified as in examples 1-4, except that steps 2 to 5 are replaced by the following steps.

2. Identification of potential genes encoding T cell antigens by using sequencing to determine the genome, exome or transcriptome of a tumor.

3. Making 384 synthetic photo-cleavable 5'-biotinylated RNAs, corresponding to fragments of the genes coding for candidate T cell antigens.

4. Distributing the synthetic RNAs into a 384-well plate, at a concentration of 0.33 μM in washing and binding buffer (100 mM Tris pH 7.4, 0.1% v/v Tween 20) and in a volume of 50 μL per well (to occupy less than ½₄th of streptavidin on beads in step 4)

5. Hydrogel beads carrying photo-cleavable 5'-biotinylated RNAs are produced by split-and-mix synthesis using a method adapted from that previously described (Zilionis et al. (2017) *Nat Protoc* 12, 44-73; Klein et al. (2015) *Cell* 161, 1187-1201). 60 μm diameter polyethylene diacrylate (PEG-DA) hydrogel beads containing streptavidin acrylamide are produced using a microfluidic device essentially as Zilionis et al. (2017) *Nat Protoc* 12, 44-73. The 160 pl droplets were produced at 4.5 KHz frequency and were exposed at 200 mW/cm² with a 365 nm UV light source (OmniCure ac475-365) to trigger gel bead polymerization. Recovered gel beads are washed 10 times with washing and binding buffer (100 mM Tris pH 7.4, 0.1% v/v Tween 20) and resuspended in the same buffer. Each bead has a binding capacity of ~$10^7$ biotinylated RNAs. One million PEG-DA-streptavidin beads are added, in a volume or 50 μL, to each well in the first column of the 384-well plate containing the synthetic photo-cleavable 5'-biotinylated RNAs and incubate for 60 mins at room temperature to allow binding. At this point less than $1/24$th of the available biotin binding sites on the beads are occupied.

6. Recovering the contents of each well, washing the beads three times with washing and binding buffer (100 mM Tris pH 7.4, 0.1% v/v Tween 20).
7. Pool the washed beads in 500 μl of with washing and binding buffer (100 mM Tris pH 7.4, 0.1% v/v Tween 20).
8. Redistribute the beads into each well of the second row of the 384-well plate.
9. Repeat steps 4 to 7, after each step re-distributing the beads into each well of the next row of the plate.
10. Recovering the contents of each well from the last row of the plate washing the beads three times with 500 μl of washing and binding buffer (100 mM Tris pH 7.4, 0.1% v/v Tween 20).
11. Pool the washed beads in 200 μl of nuclease free water. At this point each bead carries 24 different RNAs, each RNA is present on one bead in 16, but as there are $8^{24}=4.7×10^{21}$ possible permutations of the 24 RNAs on different beads every bead has a different permutation of the 24 RNAs.
12. Single B cells are co-compartmentalized in ~1 nL volume droplets with single hydrogel beads carrying RNAs and transfection reagents (Lipofectamine MessengerMAX; ThermoFisher Scientific) using a microfluidic device as described (Zilionis et al. (2017) Nat Protoc 12, 44-73). The droplets are collected in a 1.5 mL tube containing HFE-7500 and 0.1% surfactant, UV photo-cleaved for 90 seconds (OmniCure ac475-365) and incubated at room temperature for 5 mins to transfect the cells with the RNA.
13. Transfected cells are recovered by addition of 100 μL of EX-VIVO 15 supplemented with 5% human serum, followed by 100 μL of 1H, 1H,2H,2H-Perfluoro-1-octanol (370533, Sigma) and gently mixed.

Example 7. Penetratin Based Delivery of DNA Allowing mRNA Translation

Cognate pairs of tumor T cell antigens and T cell receptors are identified as in example 6, except that steps 3 and 12 are replaced by the following steps.
3. Making 384 synthetic photo-cleavable 5'-biotinylated RNAs, corresponding to fragments of the genes coding for candidate T cell antigens and coupling these to the cell penetrating peptide, penetratin.
12. Single B cells in EX-VIVO 15 are co-compartmentalized in ~1 nL volume droplets with single hydrogel beads carrying RNAs using a microfluidic device as described (Zilionis et al. (2017) Nat Protoc 12, 44-73). The droplets are collected in a 1.5 mL tube containing HFE-7500 and 0.1% surfactant, UV photo-cleaved for 90 seconds (OmniCure ac475-365) and incubated at room temperature for 5 mins to transfect the cells with the RNA.

Example 8 (Individual DNA Made on Beads and Transcribed into mRNA and Transfected in Drop)

Cognate pairs of tumor T cell antigens and T cell receptors are identified as in example 1-4, except that steps 2-5 are replaced by the following steps.
2. Identification of potential genes encoding T cell antigens by using sequencing to determine the genome, exome or transcriptome of a tumor.
3. Making 384 synthetic 5'-biotinylated DNAs, comprising fragments of the genes coding (plus strand) for T cell antigens with an upstream T7 RNA polymerase promoter.
4. Making 384 synthetic DNAs, complementary to the oligonucleotides from step 2, and annealing them to the oligonucleotides from step 2.
5. Distributing the double stranded synthetic DNAs from step 3 into a 384-well plat, at a concentration of 0.33 UM in washing and binding buffer (100 mM Tris pH 7.4, 0.1% v/v Tween 20) and in a volume of 50 μL per well (to occupy less than $1/24^{th}$ of streptavidin on beads in step 4)
6. Hydrogel beads carrying double stranded synthetic DNAs are produced by split-and-mix synthesis using a method adapted from that previously described[1,2]. 60 μm diameter Polyethylene diacrylate (PEG-DA) hydrogel beads containing streptavidin acrylamide are produced using a microfluidic device essentially as[1]. The 160 pl droplets were produced at 4.5 KHz frequency and were exposed at 200 mW/cm$^2$ with a 365 nm UV light source (OmniCure ac475-365) to trigger gel bead polymerization. Recovered gel beads are washed 10 times with washing and binding buffer (100 mM Tris pH 7.4, 0.1% v/v Tween 20) and resuspended in the same buffer. Each bead has a binding capacity of ~$10^7$ biotinylated RNAs. One million PEG-DA-streptavidin beads are added, in a volume or 50 μL, to each well in the first column of the 384-well plate containing the synthetic double stranded synthetic DNAs and incubate for 60 mins at room temperature to allow binding. At this point less than $1/24^{th}$ of the available biotin binding sites on the beads are occupied.
7. Recovering the contents of each well, washing the beads three times with washing and binding buffer (100 mM Tris pH 7.4, 0.1% v/v Tween 20).
8. Pool the washed beads in 500 μl of with washing and binding buffer (100 mM Tris pH 7.4, 0.1% v/v Tween 20).
9. Redistribute the beads into each well of the second column of the 384-well plate.
10. Repeat steps 5 to 7, after each step re-distributing the beads into each well of the next row of the plate.
11. Recovering the contents of each well from the last column of the plate washing the beads three times with 500 μl of washing and binding buffer (100 mM Tris pH 7.4, 0.1% v/v Tween 20).
12. Pool the washed beads in 200 μl of nuclease free water. At this point each bead carries 24 different DNAs, each DNA is present on one bead in 16, but as there are $8^{24}=4.7×10^{21}$ possible permutations every bead has a different permutation of the 24 DNAs.
13. Single B cells are co-compartmentalized in ~1 nL volume droplets with single hydrogel beads carrying RNAs reagents for in vitro transcription (HiScribe T7 ARCA mRNA kit, with tailing) and transfection (Lipofectamine MessengerMAX; ThermoFisher Scientific) using a microfluidic device as described[1]. The droplets are collected in a 1.5 mL tube containing HFE-7500 and 0.1% surfactant, UV photo-cleaved for 90 seconds (OmniCure ac475-365) and incubated at room temperature for 30 mins to in vitro transcribe the RNA and transfect the cells with the RNA.

14. Transfected cells are recovered by addition of 100 μL of X VIVO media supplemented with 5% human serum, followed by 100 μL of 1H, 1H,2H,2H-Perfluoro-1-octanol (370533, Sigma) and gently mixed.

Example 9 (Minigene Made on Beads and Transcribed into mRNA and Transfected in Drop)

Cognate pairs of tumor T cell antigens and T cell receptors are identified as in example 1-4, except that steps 2-5 are replaced by the following steps.

2. Identification of potential genes encoding T cell antigens by using sequencing to determine the genome, exome or transcriptome of a tumor.

3. Making 384 synthetic DNA oligonucleotides in which the mutated amino acid residues and flanking 12 amino acids on both sides are encoded by a "minigene" of 75 nucleotides that can be transcribed in vitro using T7 or T3 or SP6 RNA polymerase, where each of the genes carry a T7, SP6 or T3 RNA polymerase promoter, optionally a ribosome entry site (Kozak sequence), an initiation codon and termination signal. The RNA synthesis can include cap nucleotide analogs to further stabilize the RNA or other sequences, or features, as known by people skilled in the art (NEB, Thermo fisher website).

4. Making 384 synthetic DNAs, complementary to the oligonucleotides from step 2, and annealing them to the oligonucleotides from step 2. Annealing results in double-stranded DNA with a different 4 nucleotide 5'-overhang on each end. The first set of 16 DNAs have a first overhang complementary to the 5'-overhang present on the DNA on the hydrogel bead (see step 3) and a second overhang that is different from the first, but identical in all 16 DNAs. The second set of 16 DNAs have a first overhang complementary to the 5'-overhang present on the first set of 16 DNAs, and not identical to other 5'-overhangs, and a second overhang that is different from the first, but identical in all 16 DNAs. The third, and subsequent sets, up to the 24th set are designed in the same manner, with a first overhang complementary to the 5'-overhang present on the previous set of 16 DNAs and a second overhang that is different from the first, and not identical to other 5'-overhangs, but identical in all 16 DNAs.

5. Distributing the double stranded synthetic DNAs from step 3 into a 384-well plate in T7 DNA ligase buffer (NEB), the first set of 16 DNAs being distributed into the first column, the second set of 16 DNAs being distributed into the second column, and so on, until column 24. Each well contains 5 μl of 5 μM double-stranded DNA and T7 DNA ligase (NEB, #M0318) as per the manufacturer's instructions.

6. Hydrogel beads carrying double stranded synthetic DNAs are produced by split-and-mix synthesis using a method adapted from that previously described. 60 μm diameter Polyethylene diacrylate (PEG-DA) hydrogel beads containing streptavidin acrylamide are produced using a microfluidic device essentially as Zilionis et al. (2017) *Nat Protoc* 12, 44-73. The 160 pl droplets were produced at 4.5 kHz frequency and were exposed at 200 mW/cm$^2$ with a 365 nm UV light source (Omni-Cure ac475-365) to trigger gel bead polymerization. Recovered gel beads are washed 10 times with washing and binding buffer (100 mM Tris pH 7.4, 0.1% v/v Tween 20) and resuspended in the same buffer. Twenty four million PEG-DA beads are incubated in 1 ml final volume for 1 h at room temperature with 50 μM of a photo-cleavable biotinylated dsDNA oligonucleotide with a 5' overhang complementary to the 5'-overhang of the dsDNA oligos in the first column of the microtitre plate in step 4. One million PEG-DA-streptavidin beads coupled to the dsDNA are added to each well in the first column of the 384-well plate containing the synthetic double stranded synthetic DNAs and incubated for 60 mins at 20° C. to allow ligation.

7. Recovering the contents of each well, washing the beads as described (Zilionis et al. (2017) *Nat Protoc* 12, 44-73).

8. Pooling the washed beads and redistributing into each well of the second row of the 384-well plate.

9. Repeat steps 5 to 7, after each step re-distributing the beads into each well of the next column of the plate.

10. Recovering the contents of each well from the last column of the plate washing the beads three times with 500 μl of washing and binding buffer (100 mM Tris pH 7.4, 0.1% v/v Tween 20).

11. Pool the washed beads in 200 μl of nuclease free water. At this point each bead carries ~5×10$^7$ copies of a tandem minigene (TMG) construct with 24 different minigenes, each minigene is present on one bead in 16, but as there are 8$^{24}$=4.7×10$^{21}$ possible permutations of the minigenes every bead has a different permutation of the 24 DNAs.

12. Single B cells are co-compartmentalized in ~1 nL volume droplets with single hydrogel beads carrying the TMGs and reagents for in vitro transcription (HiScribe T7 ARCA mRNA kit, with tailing) and transfection (Lipofectamine MessengerMAX; ThermoFisher Scientific) using a microfluidic device as described[1]. The droplets are collected in a 1.5 ml tube containing HFE-7500 and 0.1% surfactant, UV photo-cleaved for 90 seconds (OmniCure ac475-365) and incubated at room temperature for 30 mins to in vitro transcribe the RNA and transfect the cells with the RNA.

13. Transfected cells are recovered by addition of 100 μL of EXVIVO15 supplemented with 5% human serum, followed by 100 μL of 1H, 1H,2H,2H-Perfluoro-1-octanol (370533, Sigma) and gently mixed.

Example 10 (Same as Above with a Different Coupling Chemistry)

As example 8 and 9, except that the hydrogel beads in step 5 are made from polyacrylamide and the photo-cleavable biotinylated dsDNA oligonucleotide carries a 5' acrydite group and is covalently coupled to the polyacrylamide during polymerisation, as described (Zilionis et al. (2017) *Nat Protoc* 12, 44-73).

Example 11 (Same as Above with a Different Reverse Transcription Reaction Chemistry)

In all examples above, the reverse transcription reaction performed in step 8 and the cDNA amplification described in step 9 can be either individually or both be replaced by a template switch reverse transcription reaction and specific amplification.

Such reaction is performed in droplet with an enzyme compatible with priming on non templated nucleotides (such as SuperScriptase 2, MutliScribe RT, SmartScribe RT, Maxima H RT), deoxynucleotide triphosphates (dNTPs), and a template switch oligo, as well as a plurality of primers.

The plurality of primers can serve as reverse transcription primers with gene specific sequence (or polydT or random sequence) at the 3' end and an universal primer sequence followed with cell specific barcode at the 5' end.

The template switch primer comprises an universal sequence and a sequence known for people skilled in the art to associate with non templated nucleotides generated during the RT by the reverse transcriptase at the 3' end of the cDNA, typically triple Cytosine.

Alternatively, the plurality of primers will serve as free floating reverse transcription primers with gene specific sequence (or polydT or random sequence) at their 3' end. The template switch primer would comprise a single cell barcode sequence and a primer sequence known for people skilled in the art to associate with non templated nucleotides generated during the RT.

The amplification of the generated cDNA includes PCR reaction, with primer priming on the universal primers on both the templates with oligos or the plurality of primers. A second round of PCR may be used for specifically amplifying only a sub set of generated cDNA.

Typical reaction includes using template switch primer at 1 or 1.5 μM concentration, 0.9M Betaine, 0.5% Igepal CA630, 1× enzyme buffer, 2800 Unit of RT enzyme, 0.4M RT primer, 0.7 mM each dNTP, 2.3 mM DTT, 6.3 mM MgCl2, 24 Units of RNase inhibitor. Reaction is performed for 1 hour at 50° C. Emulsion is then broken using Per-fluoro-octanol, cDNA are purified using AMpure Beads and processed for PCR using universal primers present on the RT primers and on the template switch oligos.

Example 12

This example statistically confirms that it is possible to identify a repertoire of TCR-antigen binding interactions by screening the binding activation between a library of cells presenting a high diversity of antigens and a highly diverse but biased population of TCR variants from a pool of primary T cells from a patient tumor.

Objective

The objective is to identify a repertoire of TCR-antigen binding interactions by screening the binding activation between a library of cells presenting a high diversity of antigens ($\sim$1-5$\cdot$10$^4$ variants, potentially including mutated epitopes) and a highly diverse but biased population of TCR variants from a pool of primary T cells ($\sim$10$^6$ cells comprising some variants representing up to a few %), for example coming from a patient tumor.

Strategy

Each T cell is compartmentalized in a droplet together with an Antigen Presenting Cell (APC). The latter may harbour a diversity of antigens (or epitopes), for example after lentiviral transduction at high Multiplicity Of Infection (MOI). Activation interactions inside droplets are measured by a fluorescence assay. Sorting upon fluorescence will lead to a population of positive T cell/APC pairs. TCRs and epitopes from the co-encapsulated APC are co-identified with a single droplet level sequencing strategy. The inventors have optimized the different parameters, notably the MOI, to obtain sufficiently low error rates (ex: 0.1%-1%) in the identification of antigen-TCR pairs.

A workflow example is presented on FIG. 1.

Experimental Parameters

N, total number of cells ($\sim$10$^6$)

n, number of clones in the total population possessing a given TCR (10$^3$-10$^5$, corresponding to 0.1% to 10% of the total population)

d, diversity of antigens (1-5$\cdot$10$^4$)

m, number of distinct antigens displayed per APC (1-10$^3$)

a, rate of technical false positives due to assay (for example sorting errors 10$^3$-10$^2$)

Derived Parameters s=1/n, sensitivity=fraction of the total population represented by a given TCR clone which we want to associate to an antigen. For example, identifying the target of a TCR displayed by 10$^3$ cells among a total population of 10$^6$ T cells would correspond to a sensitivity of s=10$^3$/10$^6$=0.1%.

f=m/d, average frequency of each antigen variant per APC (or per droplet)

l=f*n, average number of true positives in the clonal TCR population e=a*n, average number of technical false positives (measurement errors) within a TCR clonal population b=f*(l+e), average number of each negative antigen in the population measured as positive and associated to a given TCR Measurement and Error Estimation By quantifying the successful identification, it is meant estimating the probability that the following assertion is correct: Considering all T-cells with a same TCR in the positively sorted population, the antigen recognized by the TCR corresponds to the most frequent antigen found in the co-compartmentalized APCs.

The number of true positives in the sorted population follows a Poisson distribution of parameter l:

$$\rho(k, l) = e^{-l} \frac{l^k}{k!}.$$

Now, consider the true epitope to be present k times. Identification errors come from the possibility that by chance, another (negative) epitope is represented more than k times. This is in particular due to technical false positive droplets. Although each occurrence of the true epitope should be highly enriched after sorting, there is initially a very large number (typically d>10$^4$) of potentially false epitopes co-compartmentalized with each given TCR.

Occurrences of each negative epitope follows a Poisson distribution of parameter b. The probability that a given negative epitope is present strictly less than k times is given by the cumulative probability of the Poisson distribution of parameter b:

$$H(k, b) = \frac{\int_{b}^{+\infty} t^{k-1} e^{-t} dt}{(k-1)!}$$

The probability that all the d−1 negative epitopes are present less than k times is:

$$H(k,b)^{d-1}$$

The probability $\Pi_k$ that there exist a negative epitope which is represented more than k times in the sorted population associated with the TCR is then:

$$\Pi_k = 1 - H(k,b)^{d-1}$$

The probability of successful identification $\sigma$ is finally:

$$\sigma(l, b, d) = 1 - \sum_{k=0}^{+\infty} \Pi_k \rho(k, l) = \sum_{k=0}^{+\infty} \left( \frac{\int_b^{+\infty} t^{k-1} e^{-t} dt}{(k-1)!} \right)^{d-1} e^{-l} \frac{l^k}{k!}$$

It can be seen that the probability of success depends on the parameters (l,b,d).

The probability of successful identification has been calculated for a TCR present in 1% of a population of 1 million cells, for a technical error rate of 1% and an antigen diversity of 50.000, the detection error, l and b be computed as a function of m, the number of distinct antigens displayed per APC.

Figure 2:
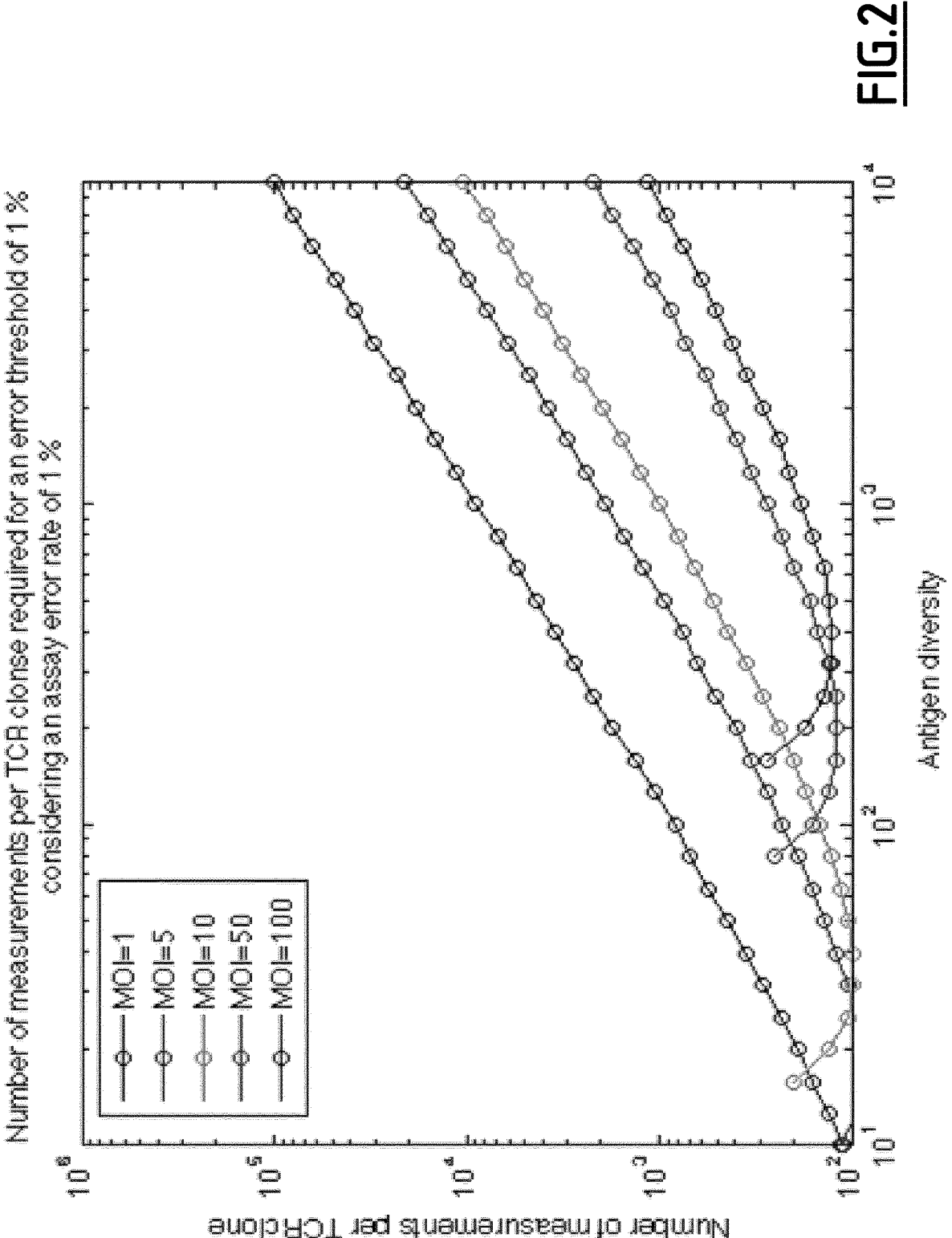
FIG. 2: Statistical analysis of number of measurements per TCR clones required to unequivocal identify the TCR recognizing a specific antigen. The number of measurement depends on the number of antigens per APC (the MOI) and the total number of antigens (the antigen diversity).

FIG. 2 shows the statistical analysis of number of measurements per TCR clones required to unequivocal identify the TCR recognizing a specific antigen. The number of measurement depends on the number of antigens per APC (the MOI) and the total number of antigens (the antigen diversity).

Figure 3:
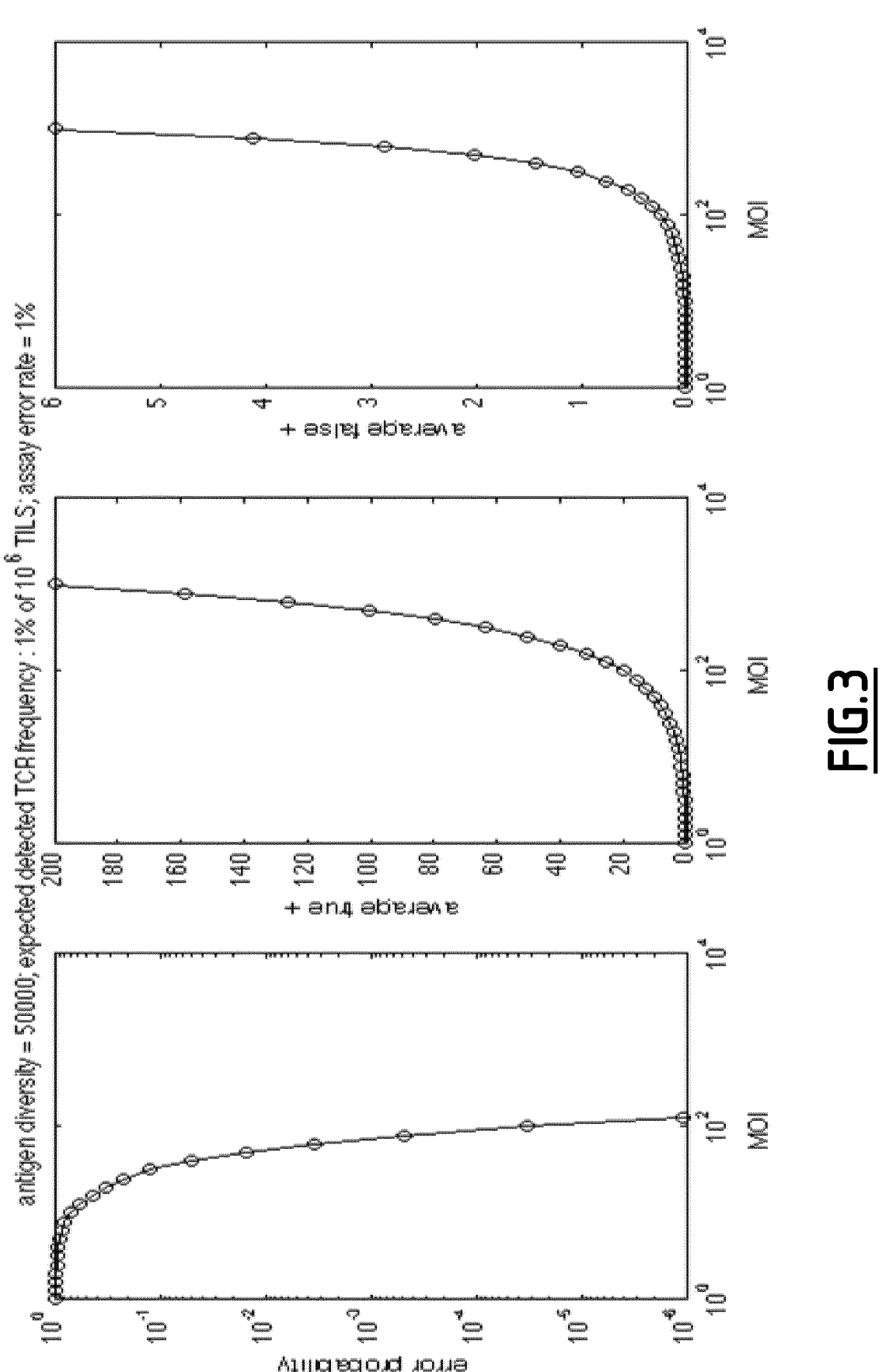
FIG. 3: Error rate of pairs mis-assignment has been calculated for typical values of the experimental parameters on the figures. From left to right: detection error/I/b computed as a function of the MOI, for a TCR present in 1% of a population of 1 million cells, for a technical error rate of 1% and an antigen diversity of 50.000.

FIG. 3 shows the error rate of pairs mis-assignment calculated for typical values of the experimental parameters on the figures. From left to right: detection error/l/b computed as a function of the MOI, for a TCR present in 1% of a population of 1 million cells, for a technical error rate of 1% and an antigen diversity of 50.000.

It was thus demonstrated that it is possible to detect TCR frequencies down to 0.1% if the epitopes diversity is typically below 10.000, using m of ~300. For higher epitopes diversity (50.000), one has to use a high m (1000) to detect 0.1% TCR frequencies, while a moderate m of 100 seems sufficient to detect 1% TCR frequencies.

The invention claimed is:

1. A method for identifying cognate pairs of a ligand species and a receptor species, comprising the following steps:
    providing a set of ligands comprising a plurality of ligand species, in which each ligand species is present more than one time;
    providing a set of receptors comprising at least one receptor species;
    compartmentalizing ligands of the set of ligands and receptors of the set of receptors to form a set of microreactors, wherein a plurality of the microreactors comprise at least one ligand species and at least one receptor species;
    assaying recognition between ligands and receptors within microreactors of the set of microreactors and, based on an assay readout within the microreactors, classifying microreactors of the set of microreactors as positive or negative, wherein a microreactor is classified as positive when at least one ligand and receptor in the microreactor recognize one with the other or as negative when no ligand and receptor recognize one with the other in the microreactor;
    identifying ligand species and receptor species contained in one or more positive microreactors;
    establishing a subset of positive microreactors each containing a first receptor species;

determining a probability that in the subset of positive microreactors containing the first receptor species, the ligand species recognized by the first receptor species corresponds to the most frequent co-compartmentalized ligand species in the subset of positive microreactors;
    if the determined probability is greater than a predetermined threshold, identifying as a cognate pair the first receptor species and the most frequent co-compartmentalized ligand species in the subset of positive microreactors.

2. The method according to claim 1, wherein the probability is determined in function of the diversity of ligand species, the average number of true positive microreactors for the subset of positive microreactors containing the first receptor species, and the average number of non-cognate ligand species contained in positive microreactors containing the first receptor species.

3. The method according to claim 2, wherein the average number of true positive microreactors for a given subset of positive microreactors containing the same receptor species, is determined according to the following expression:

$$l = fn,$$

wherein:
    l is the average number of true positive microreactors in the given subset of positive microreactors containing the same receptor species;
    n is the number of microreactors containing said receptor species; and
    f is the average frequency of each ligand species per microreactor which is determined as the ratio between a number of ligand species per microreactor and the total diversity of ligands species.

4. The method according to claim 3, wherein the average number of non-cognate ligand species contained in positive microreactors is determined according to the following expression:

$$b = f(l+e),$$

wherein:
    b is the average number of non-cognate ligand species contained in positive microreactors; and
    e is an average number of measurement errors within the subset of positive microreactors which is determined as a product of a rate of technical false positives due to the assaying and the number of microreactors containing said receptor species.

5. The method according to claim 1, wherein said probability is determined according to the following expression:

$$\sigma = \sum_{k=1}^{+\infty} \left( \frac{\int_b^{+\infty} t^{k-1} e^{-t} dt}{(k-1)!} \right)^{d-1} e^{-l} \frac{l^k}{k!},$$

wherein:
    $\sigma$ is said probability for a given subset of positive microreactors containing the same receptor species;
    d is the diversity of ligand species;
    l is the average number of true positive microreactors in the given subset of positive microreactors containing the same receptor; and
    b is the average number of non-cognate ligand species contained in positive microreactors containing the same receptor species.

6. The method according to claim 1, wherein (a) receptors of the set of receptors are expressed by one or more cells, displayed on the surface of one or more cells or one or more beads, or are in vitro encoded; or (b) ligands of the set of ligands are expressed by one or more cells or displayed on the surface of one or more cells or one or more beads, or are in vitro encoded; or both (a) and (b).

7. The method according to claim 6, wherein the recognition between ligands and receptors in each microreactor is assayed by determining if a cellular response is induced in said microreactor, wherein a microreactor is classified as positive when an induced cellular response is determined in said microreactor or as negative when no induced cellular response is determined in said microreactor.

8. The method according to claim 1, wherein the set of receptors is a set of T cell receptors (TCR) and the set of ligands is a set of T cell antigens.

9. The method according to claim 6, wherein additional reagents are added to the positive microreactors, said additional reagents comprising one or more of a reverse transcriptase (RT), a cell lysis buffer, deoxynucleoside triphospates (dNTPs), a plurality of barcoded primers specific for a nucleic acid sequence encoding ligands of the set of ligands, and a plurality of barcoded primers specific for a nucleic acid sequence encoding receptors of the set of receptors, wherein the barcoded primers specific for the ligand-encoding nucleic acid sequence comprise a primer sequence specific for the ligand-encoding nucleic acid sequence and a barcode sequence or barcode set of sequences, wherein the barcoded primers specific for the receptor-encoding nucleic acid sequence comprise a primer sequence specific for the receptor-encoding nucleic acid sequence and a barcode sequence or barcode set of sequences, and wherein the barcode sequence or barcode set of sequences contained in a microreactor is distinguishable from the barcode sequence or barcode set of sequences contained in other microreactors, but the barcoded primers specific for the ligand-encoding nucleic acid sequence and for the receptor-encoding nucleic acid sequence contained in a given microreactor carry a common barcode sequence or barcode set of sequences.

10. The method according to claim 9, wherein said barcoded primers are delivered on particles, wherein each particle carries a barcode sequence or barcode set of sequences distinguishable from barcode sequences or barcode sets of sequences carried by other particles, and each microreactor contains a single particle or between 2 to 10 particles.

11. The method according to claim 9, wherein in the positive microreactors, barcoded cDNAs are prepared by:

lysing the cells expressing or displaying receptors and/or the cells expressing or displaying ligands, to release mRNA from the cells, hybridizing at least some of the released mRNA coding for the receptor to the receptor-encoding nucleic acid sequence specific barcoded primer, and at least some of the released mRNA coding for the ligand to the ligand-encoding nucleic acid sequence specific barcoded primer, in at least some of the microreactors, reverse transcribing the released mRNA hybridized to the barcoded primers, thereby obtaining barcoded cDNAs.

12. The method according to claim 8, wherein the set of TCR and the set of T cell antigens are from a subject of interest suffering from cancer, autoimmune disease, inflammatory disease, infectious disease, or metabolic disease.

13. The method of claim 1, wherein each microreactor comprises no more than one receptor species.

14. The method according to claim 2, wherein said probability is determined according to the following expression:

$$\sigma = \sum_{k=1}^{+\infty} \left( \frac{\int_{b}^{+\infty} t^{k-1}e^{-t}dt}{(k-1)!} \right)^{d-1} e^{-l}\frac{l^{k}}{k!},$$

wherein:

$\sigma$ is said probability for the given subset of positive microreactors containing the same receptor species;

d is the diversity of ligand species;

l is the average number of true positive microreactors in the given subset of positive microreactors containing the same receptor; and b is the average number of each non-cognate ligand species contained in positive microreactors containing the same receptor species.

15. The method according to claim 3, wherein said probability is determined according to the following expression:

$$\sigma = \sum_{k=1}^{+\infty} \left( \frac{\int_{b}^{+\infty} t^{k-1}e^{-t}dt}{(k-1)!} \right)^{d-1} e^{-l}\frac{l^{k}}{k!},$$

wherein:

$\sigma$ is said probability for the given subset of positive microreactors containing the same receptor species;

d is the diversity of ligand species;

l is the average number of true positive microreactors in the given subset of positive microreactors containing the same receptor; and b is the average number of each non-cognate ligand species contained in positive microreactors containing the same receptor species.

16. The method according to claim 4, wherein said probability is determined according to the following expression:

$$\sigma = \sum_{k=1}^{+\infty} \left( \frac{\int_{b}^{+\infty} t^{k-1}e^{-t}dt}{(k-1)!} \right)^{d-1} e^{-l}\frac{l^{k}}{k!},$$

where:

$\sigma$ is said probability for the given subset of positive microreactors containing the same receptor species;

d is the diversity of ligand species;

l is the average number of true positive microreactors in the given subset of positive microreactors containing the same receptor; and b is the average number of each non-cognate ligand species contained in positive microreactors containing the same receptor species.

17. The method according to claim 1, wherein the set of receptors is a set of T cell receptors and the set of ligands is a set of T cell antigens bound to major histocompatibility complex (MHC) displayed on the surface of antigen-presenting cells (APCs).

18. The method of claim 17, further comprising obtaining the APCs by introducing a library of nucleic acids encoding T cell antigens into APCs.

19. The method of claim 17, further comprising obtaining the APCs by introducing into APCs a library of synthetic mRNAs encoding antigens, optionally wherein said mRNAs are identified by sequencing the genome, exome or transcriptome of a tumor.

20. The method according to claim 17, wherein the set of T cell receptors is displayed on the surface of T cells.

21. A method for treating cancer, inflammatory disease, autoimmune disease, infectious disease, or metabolic disease in a subject in need thereof comprising the steps of:

A) providing a set of ligands comprising a plurality of ligand species, in which each ligand species is present more than one time;

B) providing a set of receptors comprising at least one receptor species;

C) compartmentalizing ligands and receptors to form a set of microreactors, wherein a plurality of the microreactors comprise at least one ligand species and at least one receptor species;

D) assaying recognition between ligands and receptors within microreactors of the set of microreactors and, based on an assay readout within the microreactors, classifying microreactors of the set of microreactors as positive or negative, wherein a microreactor is classified as positive when at least one ligand and receptor in the microreactor recognize one with the other or as negative when no ligand and receptor recognize one with the other in the microreactor;

E) identifying ligand species and receptor species contained in one or more positive microreactors;

F) establishing a subset of positive microreactors containing a first receptor species;

G) determining a probability that in the subset of positive microreactors containing the first receptor species, the ligand species recognized by the first receptor species corresponds to the most frequent co-compartmentalized ligand species;

H) if the determined probability is greater than a predetermined threshold, identifying as a cognate pair the first receptor species and the most frequent co-compartmentalized ligand species, wherein:

(i) an antigen is identified as being part of a TCR/antigen pair, and/or (ii) a T cell expressing a TCR is identified as being part of a TCR/antigen pair, and/or (iii) a TCR is identified as being part of a TCR/antigen pair, and/or (iv) an ex-vivo engineered immune cell expressing either an antigen and/or a TCR is identified as being part of a TCR/antigen pair; and administering to the subject a therapeutically effective amount of a composition comprising said identified antigen, T cell expressing a TCR, TCR, and/or said ex-vivo engineered immune cell.

\*   \*   \*   \*   \*